United States Patent [19]

Baldwin et al.

[11] Patent Number: 4,677,115

[45] Date of Patent: Jun. 30, 1987

[54] ANTIGLAUCOMA THIENO-THIOPYRAN AND THIENO-THIEPIN SULFONAMIDE DERIVATIVES, COMPOSITIONS, AND METHOD OF USE THEREOF

[75] Inventors: John J. Baldwin, Gwynedd Valley; Marcia E. Christy, Collegeville; Gerald S. Ponticello, Lansdale, all of Pa.

[73] Assignee: Merck & Co., Inc., Rahway, N.J.

[21] Appl. No.: 863,225

[22] Filed: May 14, 1986

Related U.S. Application Data

[63] Continuation-in-part of Ser. No. 777,654, Sep. 19, 1985, which is a continuation-in-part of Ser. No. 680,684, Dec. 12, 1984, abandoned.

[51] Int. Cl.[1] .................... A61K 31/38; C07D 495/04
[52] U.S. Cl. .................................. 514/432; 514/431; 549/9; 549/23

[58] Field of Search ...................... 549/9, 23; 514/431, 514/432

[56] References Cited

U.S. PATENT DOCUMENTS 4,092,325  5/1978  Sircar et al. .................... 549/23

OTHER PUBLICATIONS

Schlessinger et al, Tetrahedron Letters No. 50, pp. 4361–4364, 1969, Pergamon Press, printed in Gr. Br.

Primary Examiner—Henry R. Jiles
Assistant Examiner—J. G. Mullins
Attorney, Agent, or Firm—William H. Nicholson; Michael C. Sudol

[57] ABSTRACT

Aromatic sulfonamides with a saturated heterocycle fused thereto are carbonic anhydrase inhibitors useful in the treatment of elevated intraocular pressure.

31 Claims, No Drawings

ANTIGLAUCOMA THIENO-THIOPYRAN AND THIENO-THIEPIN SULFONAMIDE DERIVATIVES, COMPOSITIONS, AND METHOD OF USE THEREOF

SUMMARY OF THE INVENTION

This is a continuation-in-part of copending application Ser. No. 777,654, filed Sept. 19, 1985 which in turn is a continuation-in-part of application, Ser. No. 680,684, filed Dec. 12, 1984 (now abandoned).

This invention relates to novel aromatic sulfonamides useful in the treatment of elevated intraocular pressure. More particularly this invention relates to compounds having the structural formula:

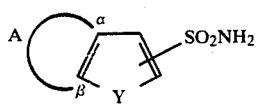

wherein A together with the two carbon atoms denoted as $\alpha$ and $\beta$ is the group:

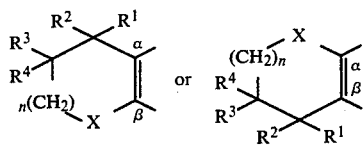

wherein $R^1$, $R^2$, $R^3$, $R^4$, X, Y and n are as hereinafter defined, as well as the pharmaceutically and ophthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2,5-thiadiazol-3-yl)oxy]-2-propanol, a $\beta$-adrenergic blocking agent, was found to reduce intraocular pressure and to be devoid of many unwanted side effects associated with pilocarpine and, in addition, to possess advantages over many other $\beta$-adrenergic blocking agents, e.g. to be devoid of local anesthetic properties, to have a long duration of activity, and to display minimal tolerance.

Although pilocarpine, physostigmine and the $\beta$-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

To be an effective and acceptable topical agent, an ophthalmic carbonic anhydrase inhibitor must not only penetrate the ophthalmic tissues to reach the active sites within the eye, but it must also be devoid of those side effects including irritation, allergic reaction and the like which would militate against long term administration.

DETAILED DESCRIPTION OF THE INVENTION

The novel compounds of this invention have structural formula:

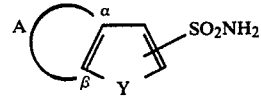

wherein A together with the two carbon atoms denoted as $\alpha$ and $\beta$ is the group:

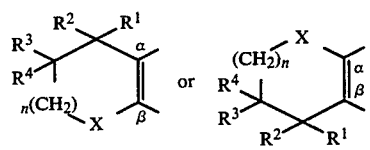

wherein:
X is —S—, —SO—, —SO$_2$— or —CH$_2$—;
Y is —S—, —O—, or —NR$^3$— wherein R$^3$ is hydrogen; C$_{1-3}$alkyl, or benzyl;
n is 1 or 2;
$R^1$, $R^2$, $R^3$, $R^4$ are independently selected from:
 (1) hydrogen,
 (2) OR$^5$ wherein R$^5$ is:
  (a) hydrogen,
  (b) C$_{1-5}$ alkyl, either unsubstituted or substituted with

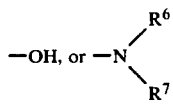

wherein $R^6$ and $R^7$ are independently hydrogen or $C_{1-5}$ alkyl, or joined together form a heterocycle with the nitrogen to which they are attached such as piperidino, morpholino, or piperazino, (c) $C_{1-5}$ alkanoyl, either unsubstituted or substituted with —OH, —NR$^6$R$^7$, —NH—COR$^8$ or —COR$^8$ wherein $R^8$ is —OH, —NR$^6$R$^7$ or $C_{1-5}$ alkoxy, (d) —CO—R$^9$, wherein $R^9$ is —NR$^6$R$^7$ or a 5- or 6-membered aromatic heterocycle such as pyridyl, imidazolyl, pyrazinyl, thiazolyl, thienyl, or oxazolyl, (3) —NR$^6$R$^7$, (4) —NHR$^{10}$ wherein $R^{10}$ is:
 (a) —SO$_2$NR$^6$R$^7$,
 (b) —SO$_2$R$^{11}$, wherein $R^{11}$ is $C_{1-5}$ alkyl, or
 (c) —CONR$^6$R$^7$, (5) $C_{1-5}$ alkyl, either unsubstituted or substituted with
 (a) —OR$^5$,
 (b) —CN,
 (c) —NR$^6$R$^7$, or
 (d) —COR$^8$, (6) —SO$_2$R$^{11}$, (7) —SO$_2$NR$^6$R$^7$, or (8) —halo, such as chloro, bromo or fluoro;

$R^1$ and $R^3$, or $R^2$ and $R^4$ taken together represent a double bond;

$R^1$ and $R^2$, or $R^3$ and $R^4$ taken together represent
 (1) =O, or
 (2) =NOR$^{12}$ wherein $R^{12}$ is hydrogen or $C_{1-3}$alkyl;
and one of the —CH$_2$— groups of —(CH$_2$)$_n$— can be substituted with —COR$^8$, —CH$_2$R$^8$, or —CH$_2$COR$^8$.

It is preferred that Y is —S—. It is also preferred that X is —S— or —SO$_2$—, n is 1, $R^2$ is hydrogen, $R^3$ and $R^4$ are hydrogen or $C_{1-5}$ alkyl and $R^1$ is —OH, —CH$_2$OH or —NR$^6$R$^7$.

Compounds of formula I which are especially preferred are:

5,6-dihydro-4H-4-hydroxythieno[2,3-b]thiopyran-2-sulfonamide-7,7-dioxide;

5,6-dihydro-4H-4-hydroxythieno[2,3-b]thiopyran-2-sulfonamide;

6,7-dihydro-5H-7-hydroxythieno[3,2-b]thiopyran-2-sulfonamide;

6,7-dihydro-5H-7-hydroxythieno[3,2-b]thiopyran-2-sulfonamide-4,4-dioxide;

5,6-dihydro-4H-4-(N-ethylamino)thieno[2,3-b]thiopyran-2-sulfonamide-7,7-dioxide;

5,6-dihydro-4H-4-aminothieno[2,3-b]thiopyran-2-sulfonamide-7,7-dioxide;

5,6-dihydro-4-hydroxy-5,5-dimethyl-4H-thieno[2,3-b]thiopyran-2-sulfonamide-7,7-dioxide;

5,6-dihydro-4H-4-hydroxymethylthieno[2,3-b]thiopyran-2-sulfonamide-7,7-dioxide;

5,6-dihydro-4-isobutylamino-4H-thieno[2,3-b]thiopyran-2-sulfonamide-7,7-dioxide; or 5,6-dihydro-4-n-butylamino-4H-thieno[2,3-b]thiopyran-2-sulfonamide-7,7-dioxide.

Substitution at $R^1$, $R^2$, $R^3$ or $R^4$ such that $R^1$ and $R^2$ are different and/or $R^3$ and $R^4$ are different produces compounds with asymmetric carbons. This invention contemplates all of the enantiomers, and diastereomers and mixtures thereof.

The nomenclature used herein is such that the following names are used for the chemical structures immediately above them:

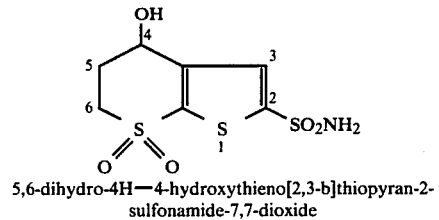

5,6-dihydro-4H—4-hydroxythieno[2,3-b]thiopyran-2-sulfonamide-7,7-dioxide

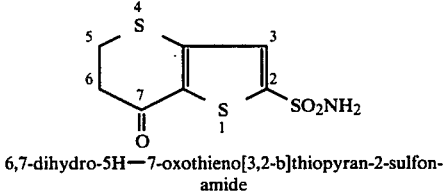

6,7-dihydro-5H—7-oxothieno[3,2-b]thiopyran-2-sulfonamide

The novel process of this invention comprises, as the last step, introduction of the sulfonamide group, which may be followed by removal of protecting groups from labile substituents, oxidations or reductions depending on the end product desired. Introduction of the sulfonamide group comprises the steps of:

1. treatment of the heteroaromatic compound with an organometallic such as n-butyl lithium, lithium phenyl, sodium naphthilide or the like in an ethereal solvent such as tetrahydrofuran (THF), diethyl ether, 1,2-dimethoxyethane or the like, especially THF, at about $-100°$ to $-25°$ C., especially about $-78°$ C., for a period of about 10 to 60 minutes especially about 30 minutes;

2. treatment with gaseous sulfur dioxide, preferably by passing it over the surface of the stirred mixture, at about $-100°$ to $-25°$ C., preferably about $-78°$ C., for about 20 to 100 minutes, preferably about 40 minutes; followed if desired by evaporation of the solvent;

3. treatment with a source of positive halogen such as N-chlorosuccinimide (NCS), N-bromosuccinimide (NBS), or the like in an inert organic solvent such as a chlorinated hydrocarbon, for example chloroform, methylene chloride, ethylene dichloride or the like; an aromatic solvent, for example, benzene, toluene or the like; or acetonitrile or the like, or aqueous sodium bicarbonate at about 0° to 40° C., preferably about 25° C. for about 1 to 6 hours; followed, if desired, by evaporation of the solvent; and 4. treatment of the heteroaromatic-sulfonyl halide, preferably a chloride, with ammonia or an ammonia precursor, for example by adding a solution of the sulfonyl halide in a water-miscible solvent such as acetone to aqueous ammonia at about 0° to 30° C. followed by extraction of the sulfonamide with an organic solvent.

An alternate procedure for introduction of the sulfonamide group comprises the steps of:

(1) treatment of the heteroaromatic compound in a chlorinated hydrocarbon such as chloroform, methylene dichloride or 1,2-dichloroethane, at about $-20°$ to 0° C. with acetic anhydride followed by dropwise addition of concentrated sulfuric acid and aging at 0° to 20° C. to produce the heteroaromatic sulfonic acid;

(2) treatment of the sulfonic acid in a chlorinated hydrocarbon, at −10° to +10° C. with a chlorinating agent such as phosphorus pentachloride to produce the heteroaromatic sulfonyl chloride; and (3) treatment of a solution of the sulfonyl chloride in an inert solvent, preferably an aqueous miscible solvent with concentrated aqueous ammonium hydroxide at about −35° to −20° C.

Following formation of the sulfonamide group, protective groups, if any may be removed. These protective groups are generally labile ethers such as a 2-methoxyethoxymethyl ether or dihydropyranyl ether of an alcohol, or ketals especially an ethylene ketal of an oxo group and are readily removed by treatment with acid in a partially aqueous medium such as a dilute mineral acid such as sulfuric or hydrochloric acid at about 15° to 100° C. for about 5 to 60 minutes.

In addition, hydroxy group may be oxidized to oxo groups with Jones reagent ($CrO_3/H_2SO_4$) or manganese dioxide in chloroform. Oxo groups may be reduced with a complex metal hydride, such as sodium borohydride. Thio groups may be oxidized to the sulfoxide with sodium metaperiodate and to the sulfone with Oxone® (potassium peroxymonosulfate, $2KHSO_5 \cdot KHSO_4 \cdot K_2SO_4$) or m-chloroperbenzoic acid or the like.

Other methods of modifying other functional groups are described in the individual examples which follow.

The novel pharmaceutical formulations of this invention are adapted for oral administration such as tablets, capsules or the like; for nasal administration, especially in the form of a spray; for injection, in the form of a sterile injectable liquid; or for topical ocular administration in the form of solutions, ointments or solid water soluble polymeric inserts.

This invention is particularly concerned with formulations adapted for topical ocular administration for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure by the administration of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

5,6-Dihydro-4H-4-hydroxythieno[2,3-b]thiopyran-2-sulfonamide-7,7-dioxide

Step A: Preparation of 5,6-dihydro-4H-4-(2-methoxyethoxymethoxy)-thieno[2,3-b]thiopyran To a solution of 5,6-dihydro-4H-thieno[2,3-b]thiopyran-4-ol (5.0 g, 0.029 mol), diisopropylethylamine (5.6 g, 0.043 mol) in $CH_2Cl_2$ (60 ml) under $N_2$ was added dropwise 2-methoxyethoxymethylchloride (5.46 g, 0.044 mol). After stirring at room temperature overnight, the solution was washed with cold 0.5N HCl (2x), saturated $NaHCO_3$ solution, dried, filtered and concentrated to dryness. The residue was chromatographed on silica gel and the product was eluted with 10% ethyl acetate/hexane (v/v) to yield 5.65 g (75%) of the desired product.

Step B: Preparation of 5,6-dihydro-4H-4-(2-methoxyethoxymethoxy)-thieno[2,3-b]thiopyran-2-sulfonamide To a flame-dried flask under $N_2$ was added the product from Step A (5.2 g, 0.02 mol) and THF (75 ml). The solution was cooled to −78° C. and a solution of 1.6M n-butyl lithium in hexane (14 ml, 0.22 mol) was added dropwise. After the addition, the suspension was stirred an additional 0.5 hour at −78° C. and then $SO_2$ gas was passed over the surface for 40 minutes. After an additional 5 minutes at −78° C., ether (400 ml) was added and the suspension was stirred at room temperature for 1 hour, and then concentrated to dryness. The residue was treated with cold $CH_2Cl_2$ (200 ml) and N-chlorosuccinimide (2.8 g, 0.021 mol) and the mixture was stirred at room temperature for 2 hours. The mixture was filtered and the filtrate concentrated to dryness. The residue was dissolved in acetone (25 ml) and the solution was added to concentrated aqueous $NH_3$ (40 ml). The acetone was removed on a rotary evaporator, the residue was treated with $H_2O$ (50 ml) and the mixture was extracted with ethyl acetate (2x). The organic extract was dried, filtered and concentrated to dryness. The residue was chromatographed on silica gel and the product eluted with 30% ethyl acetate/hexane (v/v). The residue was crystallized from acetonitrile to yield 4.1 g of product (60%), m.p. 118°–120° C.

Step C: Preparation of 5,6-dihydro-4H-4-(2-methoxyethoxymethoxy)-thieno[2,3-b]thiopyran-2-sulfonamide-7,7-dioxide To a solution of the product from Step B (3.5 g, 0.01 mol) in $CHCl_3$ (250 ml) was added dropwise a solution of 3-chloroperbenzoic acid (4.6 g, 0.021 mol) in $CHCl_3$ (250 ml). After 24 hours, the suspension was concentrated to dryness and the residue was dry packed with No. 5 activity grade alumina and chromatographed on No. 2 activity grade alumina eluting with 5% $CH_3OH/CHCl_3$ (v/v) to yield 4.35 g of product (100).

Step D: Preparation of 5,6-dihydro-4H-4-hydroxythieno[2,3-b]thiopyran-2-sulfonamide-7,7-dioxide To a solution of the product from Step C (3.5 g, 0.009 mol) in $CH_3OH$ (50 ml) was added dropwise a mixture of $H_2SO_4$ (50 ml) and $H_2O$ (50 ml). After addition the reaction mixture was poured into $H_2O$ (400 ml) and extracted with ethyl acetate (6x). The aqueous layer was basified with $NaHCO_3$ and extracted was dried, filtered, and concentrated to dryness. The residue was dry packed on silica gel and chromatographed on silica gel eluting with 10% $CH_3OH/CHCl_3$ (v/v). The eluted material was crystallized from $CH_3CN$-ether to yield 1 g of product (63%), m.p. 167°–168° C.

EXAMPLE 2

5,6-Dihydro-4H-4-oxothieno[2,3-b]thiopyran-2-sulfonamide

Step A: Preparation of 5,6-dihydro-4H-4-oxo-thieno[2,3-b]thiopyran ethylene ketal A solution of 5,6-dihydro-4H-4-oxothieno[2,3-b]thiopyran (4.5 g, 0.026 mol), benzene (75 ml), p-toluenesulfonic acid (0.25 g) and ethylene glycol (7.5 ml) was heated at reflux under a Dean Stark trap. After 18 hours, the solution was poured into saturated $Na_2CO_3$ solution, separated and the aqueous phase was extracted with $CH_2Cl_2$ (2x) The organic extracts were dried, filtered, concentrated to dryness and the residue distilled to yield the ketal (65%), b.p.$_{0.5\ mm}$, 128°–130° C.

Step B: Preparation of 5,6-dihydro-4H-4-oxo-thieno[2,3-b]thiopyran-2-sulfonamide Using substantially the same procedure described in Example 1, Step B, there was prepared the title compound from 26.2 g (0.12 mol) of product from Step A of this Example 2 except the crude ketal after the ammonia treatment was hydrolyzed in 3N HCl and acetone by heating on a steam bath for 0.5 hour. After evaporation of the acetone, the aqueous phase was extracted with ethyl acetate (3x). The organic extracts were dried, filtered and concentrated to dryness. The residue was chromatographed on silica gel and eluted with 40–50% ethyl acetate/hexane to yield 1.45 g (5%) of product from $CH_3CN$, m.p. 222°–223° C.

EXAMPLE 3

6,7-Dihydro-5H-7-oxothieno[3,2-b]thiopyran-2-sulfonamide

Step A: Preparation of 6,7-dihydro-5H-7-oxothieno[3,2-b]thiopyran ethylene ketal A solution of 6,7-dihydro-5H-7-oxothieno[3,2-b]thiopyran (5.0 g, 0.029 mol), benzene (75 ml), ethylene glycol (7.5 ml) and p-toluenesulfonic acid (0.3 g) was heated at reflux with a Dean Stark trap for removal of $H_2O$. After 4 days, the solution was cooled and washed with saturated $Na_2CO_3$ and separated. The aqueous phase was further extracted with $CH_2Cl_2$ (2x) and the combined organic extracts were dried, filtered and concentrated to dryness. The residue was chromatographed on activity 2 alumina eluting with 10% ethyl acetate/hexane (v/v) to yield 3.95 g of product (63%).

Step B: Preparation of 6,7-dihydro-5H-7-oxothieno[3,2-b]thiopyran-2-sulfonamide

Utilizing the procedure described in Example 2, Step B starting with the product of Step A, of this Example there is provided the desired product in 31% yield, m.p. 213°–214° C.

EXAMPLE 4

6,7-Dihydro-5H-7-hydroxythieno[3,2-b]thiopyran-2-sulfonamide

To a solution of 6,7-dihydro-5H-7-oxothieno[3,2-b]thiopyran-2-sulfonamide from Example 3 (3.3 g, 0.013 mol) in absolute ethanol (120 ml) was added $NaBH_4$ (0.6 g, 0.616 mol) and the mixture was heated for 0.5 hour with stirring at 60°–70° C. The mixture was then poured into $H_2O$ and extracted with ethyl acetate (4x). The organic extract was dried, filtered and concentrated to dryness to yield 3.26 g (98%) of product, m.p. 157°–158° C. ($CH_3CN$).

EXAMPLE 5

5,6-Dihydro-4H-4-hydroxythieno[2,3-b]thiopyran-2-sulfonamide

Using substantially the same procedure described in Example 4 but starting with the 4-oxo analog from Example 2, there was prepared the desired product in 95% yield with m.p. 168°–170° C. ($CH_3CN$).

EXAMPLE 6

5,6-Dihydro-4H-4-oxo-thieno[2,3-b]thiopyran-2-sulfonamide-7,7-dioxide

To a solution of 5,6-dihydro-4H-4-hydroxythieno[2,3-b]thiopyran-2-sulfonamide-7,7-dioxide (0.6 g, 0.00213 mol) in acetone (20 ml) was added Jones reagent (1 ml) and the mixture was stirred at room temperature for 10 minutes. After pouring into $H_2O$, the aqueous phase was separated and extracted with ethyl acetate (3x). The organic extracts were washed with saturated $NaHCO_3$ solution, dried, filtered and concentrated to dryness. The residue was crystallized from $CH_3CN$ to yield 0.4 g of product (67%), m.p. 242°–243° C.

EXAMPLE 7

6,7-Dihydro-5H-7-hydroxythieno[3,2-b]thiopyran-2-sulfonamide-4-oxide

To a solution of sodium metaperiodate (1.0 g, 0.0047 mol) in $H_2O$ (30 ml) was added dropwise, at room temperature, a solution of 6,7-dihydro-5H-7-hydroxythieno[3,2-b]thiopyran-2-sulfonamide (1.0 g, 0.004 mol) in $CH_3OH$ (75 ml). After stirring overnight at room temperature, the reaction mixture was concentrated to dryness, and the residue was dry packed on silica gel, placed on a column of silica gel and the product eluted with 10% $CH_3OH/CHCl_3$ (v/v) to give 0.95 g (89%) of product; m.p. 190°–200° C. ($CH_3OH$-isopropyl alcohol).

Analysis calc'd for $C_7H_9NO_4S_3$: N, 5.24; C, 31.44; H, 3.39. Found: N, 5.64; C, 31.59; H, 3.41.

EXAMPLE 8

5,6-Dihydro-4H-4-hydroxythieno[2,3-b]thiopyran-2-sulfonamide-7-oxide

Using the procedure substantially as described in Example 7, but starting with 5,6-dihydro-4-hydroxythieno[2,3-b]thiopyran-2-sulfonamide there is produced the corresponding 7-oxide in 53% yield, m.p. 155°–174° C.

Analysis calc'd for $C_7H_9NO_4S_3$: N, 5.24; C, 31.44; H, 3.39. Found: N, 5.08; C, 31.63; H, 3.28.

EXAMPLE 9

6,7-Dihydro-5H-7-hydroxythieno[3,2-b]thiopyran-2-sulfonamide-4,4-dioxide

A solution of 6,7-dihydro-5H-7-hydroxythieno[3,2-b]thiopyran-2-sulfonamide (2.65 g, 0.01 mol), acetic acid (27 ml) and 30% $H_2O_2$ (2.7 ml, 0.24 mol) was heated at 100° C. for 1 hour. After cooling to room temperature, the solution was dry packed on silica gel, placed on a column of silica gel and the product was eluted with 7.5% CH$_3$OH/CHCl$_3$ (v/v) to yield 1.4 g (49%) of product; m.p. 163°–165° C. (CH$_3$OH-CHCl$_3$).

EXAMPLE 10

6,7-Dihydro-5H-7-oxo-thieno[3,2-b]thiopyran-2-sulfonamide-4,4-dioxide

To a solution of 5,6-Dihydro-7-hydroxythieno[3,2-b]thiopyran-2-sulfonamide (2.0 g, 0.008 mol) in CH$_3$OH (100 ml) was added dropwise, at room temperature, a solution of 3-chloroperbenzoic acid (4.0 g, 0.02 mol) in CHCl$_3$ (100 ml). After stirring overnight, the mixture was concentrated to dryness. The residue was treated with acetone (75 ml) and Jones reagent (6 ml) was added with stirring. After 15 minutes, H$_2$O was added and the mixture was extracted with ethyl acetate (4x). The organic extracts were dried, filtered and concentrated to dryness. The residue was dry packed in activity 5 alumina, placed in a column of activity 2 alumina, and eluted with 20–70% CH$_3$OH/CHCl$_3$ (v/v) to yield 0.9 g (41%) of product; m.p.265°–268° C. (CH$_3$OH-CH$_3$CN).

EXAMPLE 11

5,6-Dihydro-4H-5-hydroxythieno[2,3-b]thiopyran-2-sulfonamide-7,7-dioxide

Step A: Preparation of 5,6-dihydro-4H-thieno[2,3-b]thiopyran-5-ol

To a solution of 6H-thieno[2,3-b]thiopyran (4.35 g, 0.028 mol) in THF (90 ml) under N$_2$ was added at room temperature with stirring a solution of 1M BH$_3$ in THF (60 ml, 60 mmol). After 18 hours, H$_2$O (4.35 ml) was added dropwise, then 3N NaOH (11 ml) and 30% H$_2$O$_2$ (3.2 ml, 0.028 mol). After 2 hours, the mixture was poured into H$_2$O and extracted with ethyl acetate (3x). The organic extracted were washed with saturated NaCl, dried, filtered and concentrated to dryness to yield a mixture of 5,6-dihydro-4H-4(and 5)-hydroxythieno[2,3-b]thiopyran. The residue was treated with CHCl$_3$ (150 ml), MnO$_2$ (26 g) and the mixture was stirred at room temperature overnight. The dark suspension was then filtered through a filter aid and the filtrate was concentrated to dryness. The residue was chromatographed on silica gel eluting with 15% ethyl acetate/hexane (v/v) to yield 1.0 g of 5,6-dihydro-4H-4-oxothieno[2,3-b]thiopyran and then 1.5 g of the desired product (31%).

Step B: Preparation of 5,6-dihydro-4H-5-(2-methoxyethoxymethoxy)-thieno[2,3-b]thiopyran To a solution of the 5-hydroxy compound from Step A (4.0 g, 0.023 mol), CH$_2$Cl$_2$ (55 ml) and diisopropylethylamine (4.6 g, 0.036 mol) was added, under N$_2$, dropwise, 2-methoxyethoxymethylchloride (4.3 g, 0.034 mol). After 3 days the reaction was poured into CH$_2$Cl$_2$ (200 ml) and washed with cold 1N HCl (2x). The aqueous phase was backwashed with CH$_2$Cl$_2$. The organic extracts were washed with saturated NaHCO$_3$ solution, dried, filtered and concentrated to dryness to yield 5.85 g (97.5%) of product.

Step C: Preparation of 5,6-dihydro-4H-5-(2-methoxyethoxymethoxy)-thieno[2,3-b]thiopyran-2-sulfonamide To a solution of the product from Step B (5.85 g, 0.023 mol) in THF (100 ml) under N$_2$ was added 1.6M n-butyl lithium in hexane (17 ml, 0.027 mol) at −78° C. After stirring for 0.5 hour, SO$_2$ gas was passed over the surface for 45 minutes at −78° C., then ether (800 ml) was added and the mixture was stirred for 1 hour at room temperature. The suspension was concentrated to dryness, the residue treated with saturated NaHCO$_3$ solution (100 ml), cooled in an ice bath with stirring and treated with N-chlorosuccinimide (3.3 g, 0.025 mol). After stirring at room temperature for 15 minutes, the solution was extracted with ethyl acetate (2x). The organic extracts were dried, filtered and concentrated to dryness. The residue was dissolved in acetone (50 ml) and added to concentrated aqueous NH$_3$ (50 ml). The acetone was evaporated and the aqueous layer was extracted with ethyl acetate (2x). The orgaic extracts were dried, filtered, and concentrated to dryness to yield 8.0 g (100%) of crude product.

Step D: Preparation of 5,6-dihydro-4H-5-hydroxythieno[2,3-b]thiopyran-2-sulfonamide-7,7-dioxide To a solution of product from Step C (8.0 g, 0.0225 mol) in CH$_3$OH (150 ml) was added with stirring at room temperature a solution of OXONE ® (18 g, 0.029 mol) in H$_2$O (150 ml). After 2 days, the suspension was filtered and the solid washed with CH$_3$OH. The CH$_3$OH was evaporated from the filtrate and the aqueous layer was extracted with ethyl acetate (3x). The organic extracts were dried, filtered and concentrated to dryness to yield 8.6 g of crude product. The residue was dry packed on silica gel, chromatographed on silica gel and eluted with 5% CH$_3$OH/CHCl$_3$ (v/v) to yield 2.8 g of crude 2-methoxyethoxymethyl ether of the product and 1.0 g of crude product. The ether (2.8 g) was dissolved in CH$_3$OH (50 ml) and treated with a cooled solution of H$_2$SO$_4$ (50 ml) and H$_2$O (50 ml). After stirring for 0.5 hour at room temperature, the solution was poured into H$_2$O and extracted with ethyl acetate (5x). The organic extracts were washed with saturated NaHCO$_3$ solution, saturated NaCl solution, dried, filtered and concentrated to dryness. A total of 3.0 g of crude product was obtained. This material was then treated with MnO$_2$ (10 g), OXONE ® (5.0 g) and acetone (100 ml) and the mixture was stirred at room temperature overnight. After 18 hours, the mixture was filtered through a filter aid and the pad was washed with acetone and the filtrate was concentrated to dryness. The residue was dry packed on silica gel, and chromatographed on silica gel by elution with 5% CH$_3$OH/CHCl$_3$ (v/v) to yield 0.75 g (12%) of product; m.p. 172°–176° C. (CH$_3$OH/CHCl$_3$).

EXAMPLE 12

5,6-Dihydro-4H-4-aminothieno[2,3-b]thiopyran-2-sulfonamide

Under N$_2$ a mixture of 5,6-dihydro-4H-4-oxo-thieno[2,3-b]thiopyran from Example 2 (5.0 g, 0.02 mol), ammonium acetate (15.4 g, 0.2 mol), CH$_3$OH (150 ml) and NaCNBH$_3$ (1.6 g, 0.025 mol) was stirred at room temperature. After 18 hours, acetic acid (30 ml) was added and the mixture stirred overnight after which additional NaCNBH$_3$ (1.5 g, 0.025 mol) was added. After 18 hours, 12N HCl was added, and the resulting mixture adjusted to pH 8.9 with solid Na$_2$CO$_3$, and the aqueous phase was extracted with ethyl acetate (4x). The organic extracts were dried, filtered and concentrated to dryness. The residue was dry packed, and chromatographed on silica gel and the product eluted with 20% $CH_3OH/CHCl_3$ (v/v) to yield 1.8 g of product. The solid was converted to the HCl salt with HCl-ethanol and the product was crystallized from $CH_3CN$ to yield 2.0 g (40%) as the HCl salt of the product; m.p. 254°–256° C. The free base has m.p. 155°–156° C.

EXAMPLE 13

5,6-Dihydro-4H-4-methoxythieno[2,3-b]thiopyran-2-sulfonamide

To a solution of 5,6-dihydro-4H-4-oxothieno[2,3-b]thiopyran-2-sulfonamide (38.5 g, 0.15 mol) in absolute ethanol (1.75 L) was added $NaBH_4$ (6 g, 0.16 mol) and the mixture was heated on a steam bath for 1 hour. After cooling, the ethanol was removed in vacuo and the resulting aqueous layer was acidified with 3N HCl. The aqueous phase was extracted with ethyl acetate (4x). The organic extracts were dried, filtered and concentrated to dryness. The residue was crystallized from $CH_3OH$-$CH_3CN$. After standing 3 days, TLC indicated that two products were formed in the methanolic solution which was found to be acidic. The solution was concentrated to dryness and the residue treated with saturated $NaHCO_3$ solution and extracted with ethyl acetate (3x). The organic extracts were dried, filtered and concentrated to dryness. The residue was dry packed, and chromatographed on silica gel eluting with 30% ethyl acetate/hexane (v/v) to yield 4.7 g (12%) of product; m.p. 138°–142° C. ($CH_3CN$).

Analysis calc'd for $C_8H_{11}HO_3S_3$: N, 5.28; C, 36.20; H, 4.18. Found: N, 5.56; C, 36.30; H, 3.93.

EXAMPLE 14

5,6-Dihydro-4H-4-methoxythieno[2,3-b]thiopyran-2-sulfonamide-7,7-dioxide

To a solution of the product from Example 13 (6.3 g, 0.023 mol) in $CH_3OH$ (100 ml) was added a solution of OXONE ® (17.5 g, 0.029 mol) in $H_2O$ (100 ml). After 3 days, the suspension was filtered, the solid washed with $CH_3OH$ and the $CH_3OH$ in the filtrate was removed in vacuo. The aqueous layer was extracted with ethyl acetate (3x). The organic extracts were washed with saturated NaCl, dried, filtered and concentrated to dryness. The residue was dry packed, and chromatographed on silica gel by elution with 40–60% ethyl acetate/hexane (v/v) to yield 4.1 g (60%) of product, m.p. 145°–147° C. ($CH_3OH$-$CHCl_3$).

EXAMPLE 15

6,7-Dihydro-5H-6-hydroxythieno-[3,2-b]thiopyran-2-sulfonamide-4,4-dioxide

Step A: Preparation of 6,7-Dihydro-5H-thieno[3,2-b]thiopyran-6-ol

Under $N_2$, a solution of 5H-thieno[3,2-b]thiopyran (7.2 g, 0.0468 mole) (I. Degani, et al., Ann. Chim. (Rome), 58, 263 (1968)) in dry, peroxide-free, THF (140 ml) was stirred at room temperature while 95 ml of 1M borane in THF was added rapidly dropwise. Stirring was continued for 20 hours. The solution then was cooled to 15°–20° C. and successive dropwise additions of water (7.2 ml), aqueous 3N NaOH (18 ml) and 30% $H_2O_2$ (5.3 ml) were made. After 3 hours at room temperature, the mixture was poured into water (about 1 L) and extracted with ethyl acetate (3×250 ml). The washed and dried extract was concentrated in vacuo to yield 7.85 g of a mixture of the desired compound and 6,7-dihydro-5H-thieno[3,2-b]thiopyran-7-ol.

This material was combined with 4.6 g of a comparable mixture from a previous 0.027 mole run, dissolved in $CHCl_3$ (300 ml), and treated with activated $MnO_2$ (63 g). The resulting mixture was stirred at room temperature for 24 hours and then filtered through a filter aid. Evaporation of the filtrate under reduced pressure left 10.35 g of a crude mixture of product and 6,7-dihydro-5H-thieno[3,2-b]thiopyran-7-one as a dark brown oil. This material was chromatographed on silica gel (500 g), eluting with 85 hexane/15 ethyl acetate (v/v). Chromatographic fractions containing the more polar component were pooled and concentrated to yield 3.6 g (28%) of product as a dark yellow oil that was characterized by nmr.

Step B: Preparation of 6,7-Dihydro-5H-6-(2-methoxyethoxymethoxy)-thieno[3,2-b]thiopyran Under $N_2$, a solution of product from Step A (3.6 g, 0.02 mole) and di-isopropylethylamine (5 ml) in $CH_2Cl_2$ (50 ml) was stirred while a solution of 2-methoxyethoxymethyl chloride (3.2 ml) in $CH_2Cl_2$ (7 ml) was added dropwise. Stirring was continued at room temperature for 40 hours. The solution then was washed with cold 1N HCl, cold water, cold saturated $NaHCO_3$ solution and cold water. The dried ($Na_2SO_4$) extract was concentrated in vacuo to 5.0 g of brown oil that was purified by chromatography on silica gel (250 g). Elution with 85 hexane/15 ethyl acetate (v/v) gave 3.0 g (57%) of product as an oil that was characterized by nmr.

Step C: Preparation of 6,7-dihydro-5H-6-(2-methoxyethoxymethoxy)-7H-thieno[3,2-b]-thiopyran-2-sulfonamide The product from Step B (9.2 g mmol) was sulfamoylated by the procedure described in Example 1, Step B. The crude product (2.75 g) was obtained in 88% yield as a brown oil that was purified by chromatography on silica gel (150 g). Elution with 50 ethyl acetate/50 hexane (v/v) gave 2.08 g (67%) of product as a pale yellow oil that was characterized by nmr.

Step D: Preparation of 6,7-dihydro-5H-6-hydroxythieno[3,2-b]thiopyran-2-sulfonamide-4,4-dioxide A solution of product from Step C (1.7 g, 0.005 mole) in $CH_3OH$ (35 ml) was stirred at room temperature while a solution of OXONE ® (3.85 g, 0.00625 mole) in water (30 ml) was added dropwise. The resulting suspension was stirred at room temperature overnight. The precipitate was filtered and washed with $CH_3OH$. The filtrate was concentrated in vacuo and the residual mixture extracted with ethyl acetate. Evaporation of the dried (anhydrous $Na_2SO_4$) extract left 1.85 g of a glass that was dissolved in $CH_3OH$ (25 ml). This solution was added dropwise to a stirred solution of concentrated $H_2SO_4$ (25 ml) and $H_2O$ (25 ml) at 20° C. After another 20 minutes at ambient temperature, the mixture was poured into $H_2O$ (200 ml) and extracted with ethyl acetate (4×60 ml). The aqueous phase was neutralized with solid $NaHCO_3$ and extracted again with ethyl acetate (3×50 ml). The combined ethyl acetate extracts were dried (anhydrous $Na_2SO_4$), filtered, and evaporated in vacuo. The residual 1.4 g of crude product was chromatographed on silica gel (120 g). Elution with 80 ethyl acetate/20 hexane (v/v) gave the product as a colorless glass that solidified on trituration with 10% $CH_3OH/CHCl_3$ (v/v). Recrystallization of the collected solid from CH$_3$OH yielded 0.64 g (46%) of product; m.p. 186°–188°.

Anal. calc'd for C$_7$H$_9$NO$_5$S$_3$: C, 29.67; H, 3.20; N, 4.94 Found: C, 29.82; H, 3.30; N, 4.79.

EXAMPLE 16

5,6,7,8-Tetrahydrothieno[3,2-b]thiepin-8-hydroxy-2-sulfonamide 4,4-dioxide

Step A: Preparation of 8-Hydroxy-5,6,7,8-tetrahydrothieno[3,2-b]thiepin

A solution of sodium borohydride (0.83 g, 0.022 mol) in absolute ethanol (55 ml) was added over thirty minutes to a stirred solution of 5,6,7,8-tetrahydrothieno[3,2-b]thiepin-8-one (3.65 g, 0.020 mole) in absolute ethanol (115 ml) under nitrogen at ambient temperature. After the addition, the mixture was heated at 70° C. for 1.5 hours and then concentrated under reduced pressure. Water (150 ml) was added to the residue and the mixture was extracted with ethyl acetate (3×150 ml). After drying over sodium sulfate, the solvent was evaporated under reduced pressure to yield a solid product weighing 3.63 g (97%).

An analytical sample melted at 97°–98° C. after recrystallization from hexane.

Step B: Preparation of 8-(2-methoxyethoxymethoxy)-5,6,7,8-tetrahydrothieno[3,2-b]-thiepin To a solution of 8-hydroxy-5,6,7,8-tetrahydrothieno[3,2-b]thiepin (16.6 g, 0.089 mole) and diisopropylethylamine (18.1 g, 0.14 mole) in methylene chloride (185 ml) was added β-methoxyethoxymethyl chloride (17.5 g, 0.14 mole) over 10 minutes under nitrogen at ambient temperature. The solution was stirred for 117 hours and then washed with cold 0.5N HCl (2×100 ml), saturated sodium bicarbonate solution, twice with water and dried over sodium sulfate. The solvent was evaporated under reduced pressure and the residue was chromatographed on silica gel (2.5 kg), eluting with 20% ethyl acetate-hexane (v/v), to yield 19.97 g (82%) of oily product.

Step C: Preparation of 8-(2-methoxyethoxymethoxy)-5,6,7,8-tetrahydrothieno[3,2-b]-thiepin-2-sulfonamide A solution of 8-(2-methoxyethoxymethoxy)-5,6,7,8-tetrahydrothieno[3,2-b]thiepin (19.95 g, 0.073 mole) in dry tetrahydrofuran (70 ml) was cooled to −20° C. under nitrogen and 1.6M n-butyllithium in hexane (51.3 ml, 0.082 m) was added over 30 minutes, maintaining the temperature at −15° to −10° C. After stirring at −20° C. for 1 hour, sulfur dioxide was passed over the surface of the reaction mixture for 1 hour, keeping the temperature at −10° to 0° C. The mixture was concentrated under reduced pressure below 50° C. and the residue was dissolved in methylene chloride (210 ml), cooled to 0° C., and stirred while N-chlorosuccinimide (10.95 g, 0.082 m) was added over 20 minutes. After stirring at ambient temperature for 2 hours, the mixture was filtered and the filtrate was concentrated under reduced pressure below 50° C. The oily residue was dissolved in acetone (210 ml), the solution was cooled to 0° C. and concentrated ammonium hydroxide (105 ml) was added over 10 minutes. After stirring at ambient temperature for 30 minutes, the solvent was evaporated under reduced pressure. The residue was dissolved in 0.5M potassium hydroxide (480 ml), washed with methylene chloride (2×250 ml), acidified with 6N HCl, and extracted with ethyl acetate (3×400 ml). After washing with water and drying over sodium sulfate, the solvent was evaporated under reduced pressure to give 18.07 g (70%) of tan solid product.

An analytical sample was prepared by recrystallization from nitromethane, m.p. 128°–129° C.

Step D: 8-(2-methoxyethoxymethoxy)-5,6,7,8-tetrahydrothieno[3,2-b]-thiepin-2-sulfonamide-4,4-dioxide A solution of OXONE® (28.9 g, 0.047 mole) in water (200 ml) was added to a stirred suspension of 8-(2-methoxyethoxymethoxy)-5,6,7,8-tetrahydrothieno[3,2-b]thiepin-2-sulfonamide (14.0 g, 0.040 mole) in methanol (250 ml) and the mixture was stirred at ambient temperature for 41 hours. Methanol was evaporated under reduced pressure and the aqueous suspension was extracted with ethyl acetate (3×250 ml). The combined extracts were washed twice with water, dried over sodium sulfate and evaporated under reduced pressure to give 16.62 g (theory 15.42 g) of solvated oily product which was used in the next step without further purification.

Step E: 5,6,7,8-tetrahydrothieno[3,2-b]thiepin-8-hydroxy-2-sulfonamide-4,4-dioxide A solution of concentrated sulfuric acid (200 ml) in water (200 ml) was added to a stirred solution of 8-(2-methoxyethoxymethoxy)-5,6,7,8-tetrahydrothieno[3,2-b]-2-sulfonamide-4,4-dioxide (15.42 g, 0.040 mole) in methanol (200 ml) over twenty minutes at ambient temperature. After stirring for an additional 20 minutes, approximately 50–100 ml of methanol was evaporated under reduced pressure below 55° C. Water (1000 ml) was added and the mixture was extracted with ethyl acetate (3×700 ml). The combined extracts were washed with water, saturated sodium bicarbonate solution, twice with water, dried over sodium sulfate and concentrated under reduced pressure to yield 9.63 g (81%) of product.

An analytical sample was prepared by chromatography on silica gel, eluting with 10% methanol-chloroform (v/v). The product had m.p. 201°–202° C. after recrystallization from nitromethane.

EXAMPLE 17

5,6,7,8-Tetrahydrothieno[3,2-b]thiepin-8-oxo-2-sulfonamide-4,4-dioxide

Employing the procedure substantially as described in Example 6, but using as starting material 5,6,7,8-tetrahydrothieno[3,2-b]-8-hydroxy-2-sulfonamide-4,4-dioxide from Example 16 there is produced the subject compound, m.p. 165°–166° C.

EXAMPLE 18

4,5,6,7-Tetrahydro-4-oxo-thieno[2,3-b]thiepin-2-sulfonamide-8,8-dioxide, and
4,5,6,7-tetrahydro-4-hydroxythieno[2,3-b]-thiepin-2-sulfonamide-8,8-dioxide Step A: Preparation of 4,5,6,7-tetrahydro-4-oxothieno-[2,3-b]thiepin A mixture of 4-(2-thienylthio)butyric acid (5.00 g, 0.025 mole), SUPER-CEL® (5 g) and phosphorous pentoxide (8 g) in toluene (80 ml) was vigorously stirred under nitrogen while heating at 100° C. After 2 hours, additional phosphorous pentoxide (8 g) was added and the mixture was heated for 3 hours more. After filtering the hot mixture, the solid was washed with hot toluene (3×80 ml) and the combined filtrate and washings were concentrated under reduced pressure yielding 2.52 g (55%) of product.

An analytical sample prepared by recrystallization from hexane had m.p. 53°–54° C.

Step B: Preparation of 4-oxo-4,5,6,7-tetrahydro thieno-[2,3-b]thiepin-2-sulfonamide Acetic anhydride (39.82 g, 0.39 mole) was added to a solution of 4-oxo-4,5,6,7-tetrahydro thieno[2,3-b]thiepin (24.65 g, 0.13 mole) in ethyl acetate (250 ml) and the mixture was cooled in an ice bath while a solution of concentrated sulfuric acid (13.73 g, 0.14 m) in ethyl acetate (66 ml) was added over 20 minutes. The mixture was stirred at ambient temperature for 2 hours, then cooled in an ice bath while a solution of potassium acetate (13.74 g, 0.14 mole) in 95% ethanol (81 ml) was added over 20 minutes. After stirring at ambient temperature for 1 hour, the solid was collected and dried to yield 34.13 g (87%) of potassium 4,5,6,7-tetrahydro-thieno[2,3-b]thiepin-4-oxo-2-sulfonate.

A portion of this product (10.00 g, 0.033 mole) was suspended in acetonitrile (175 ml), 18-crown-6 (1,4,7,10,13,16-hexaoxacyclooctadecane) (0.5 g) was added, followed by phosphorous pentachloride (10.41 g, 0.050 mole) and the mixture was stirred at ambient temperature for 17 hours. The solvent was evaporated under reduced pressure, the residue was extracted with methylene chloride (300 ml), filtered and the filtrate was evaporated under reduced pressure. The oily residue was dissolved in acetone (110 ml), cooled in an ice bath and stirred while concentrated ammonium hydroxide (55 ml) was added over 15 minutes. After stirring at ambient temperature for 1 hour, the mixture was concentrated under reduced pressure. The residue was treated with 0.5M potassium hydroxide (300 ml), washed with methylene chloride (2×100 ml), acidified with 6N hydrochloric acid, and extracted with ethyl acetate (3×350 ml). After washing with water and drying over sodium sulfate, the solvent was evaporated under reduced pressure to give 5.04 g (58%) of crude product which was purified by chromatography on silica gel, eluting with 10% methanol-chloroform (v/v).

An analytical sample was prepared by recrystallization from nitromethane, m.p. 185°–186° C.

Step C: Preparation of 4-oxo-4,5,6,7-tetrahydrothieno[2,3-b]thiepin-2-sulfonamide-8,8-dioxide A solution of OXONE® (13.6 g, 0.022 mole) in water (95 ml) was added to a stirred suspension of 4-oxo-4,5,6,7-tetrahydrothieno[2,3-b]thiepin-2-sulfonamide (5.10 g, 0.019 mole) in methanol (120 ml) over 20 minutes and the mixture was stirred at ambient temperature. After 92 hours, an additional 3.4 g of OXONE® dissolved in water (25 ml) was added over 10 minutes and stirring was continued for 43 hours more. Methanol was evaporated under reduced pressure and the aqueous suspension was extracted with ethyl acetate (3×200 ml). After washing twice with water and drying over sodium sulfate, the solvent was concentrated under reduced pressure and the solid residue was recrystallized from nitromethane to give 4.79 g (85%) of product melting at 197.5°–198.5° C.

An analytical sample was prepared by recrystallization from nitromethane, m.p. 198.5°–199.5° C.

Step D: Preparation of 4-hydroxy-4,5,6,7-tetrahydrothieno-[2,3-b]thiepin-2-sulfonamide-8,8-dioxide A solution of sodium borohydride (0.38 g, 0.010 mole) in ethanol (25 ml) was added over thirty minutes to a stirred suspension of 4-oxo-4,5,6,7-tetrahydro-thieno[2,3-b]thiepin-2-sulfonamide-8,8-dioxide (2.50 g, 0.0085 mole) in ethanol (60 ml) under nitrogen. The mixture was stirred at 70° C. for 2 hours, then an additional 0.15 g (0.004 mole) of sodium borohydride dissolved in ethanol (10 ml) was added over 10 minutes. After stirring at 70° C. for 2 hours more and then at ambient temperature for 15 hours, water (50 ml) was added. The mixture was acidified by the dropwise addition of 6N hydrochloric acid (5 ml) and the ethanol was evaporated under reduced pressure. The aqueous suspension was extracted with ethyl acetate (100 ml) and 2×75 ml), the combined extracts were washed with saturated sodium bicarbonate solution, twice with water, dried over sodium sulfate and evaporated under reduced pressure to yield 2.37 g (94%) of product. Further purification was effected by chromatography on silica gel, eluting with 10% methanol-chloroform (v/v)

An analytical sample was prepared by recrystallization from nitromethane, m.p. 193°–194° C.

EXAMPLE 19

(R)- and (S)-5,6-Dihydro-4H-4-hydroxythieno[2,3-b]thiopyran-2-sulfonamide-7,7-dioxide

Step A: Preparation of (S,R) and (R,R)-5,6-dihydro-4-[2-methoxy-2-phenylacetoxy]-thieno[2,3-b]thiopyran-2-sulfonamide-7,7-dioxide Dimethylaminopyridine (320 mg, 2.62 mmol), 5,6-dihydro-4H-4-hydroxythieno[2,3-b]thiopyran-2-sulfonamide-7,7-dioxide (4.95 g, 17.5 mmol), and (R)-α-methoxyphenylacetic acid (4.36 g, 26.3 mmol) were dissolved in THF (100 ml), then dicyclohexylcarbodiimide (5.4 g, 26.3 mmol) was added and the mixture stirred at room temperature overnight. Dicyclohexylurea was removed by filtration and washed with THF. The filtrate and the wash were combined, the solvent was removed in vacuo and the residue was chromatographed on a silica gel 60 column by elution with ethylacetate/hexanes (60/40 v/v) to yield 1.69 g of (S,R)-diastereomer and 1.43 g of (R,R)-diastereomer, the (S,R)-diastereomer coming off the column first. The other fractions containing both diastereomers were combined (2.0 g) and rechromatographed on a silica gel 60 column as above yielding 670 mg of (S,R)- and 970 mg of (R,R)-diastereomer. The melting point of the (S,R)-diastereomer, after crystallization from THF-hexanes, was 160°–61° C. and that of the (R,R) diastereomer was 173°–4° C.

$[\alpha]_D^{20°}$ of (S,R)-diastereomer; −331 (c=1, THF).
$[\alpha]_D^{20°}$ of (R,R) diastereomer; +6.4 (c=1, THF).

Step B: Preparation of (R)-5,6-dihydro-4H-4-hydroxythieno[2,3-b]thiopyran-2-sulfonamide-7,7-dioxide The (R,R)-diastereomer (6.0 g, 13.9 mmol) was stirred in 0.2N NaOH (290 ml) for 1 hour. The pH of the solution was adjusted to 7.0 with 3N HCl and extracted with ethyl acetate (3×300 ml). The extracts were combined and the solvent was removed in vacuo. The crude product was crystallized from 15 ml of hot CH₃CN yielding 3.1 g (79%) of product, m.p. 170°–171° C.

Anal. calcd. for C₇H₉NO₅S₃: C, 29.68; H, 3.20; N, 4.95. Found: C, 29.87; H, 3.24; N, 5.00.

$[\alpha]_D^{20}$: −16.0 (c=1, CH₃OH).

Step C: Preparation of (S)-5,6-dihydro-4H-4-hydroxythieno[2,3-b]thiopyran-2-sulfonamide 7,7-dioxide The (S)-isomer was prepared in an analogous manner from the (S,R)-diastereomer: m.p. 170°–71° C.

Anal. Calcd for C₇H₉NO₅S₃: C, 29.68; H, 3.20; N, 4.95. Found: C, 29.60; H, 3.07; N, 4.86

$[\alpha]_D^{20}$ = +16.0 (c=1, CH₃OH)

EXAMPLE 20

4-Hydroxy-4,5,6,7-tetrahydrobenzo[b]-thiophene-2-sulfonamide

Step A: Preparation of 4-hydroxy-4,5,6,7-tetrahydrobenzo[b]thiophene

A solution of 20 g (0.13 mol) of 4,5,6,7-tetrahydro-4-oxo-benzo[b]thiophene in 300 ml absolute ethanol was stirred with 5.4 g (0.14 mol) NaBH₄ at ambient temperature for 20 hours. Then 200 ml H₂O was added and the ethanol was removed under reduced pressure. The resulting mixture was extracted with ether. The combined organic extracts were backwashed with H₂O, dried (Na₂SO₄), filtered, and evaporated under reduced pressure. The resultant colorless solid was triturated with hexane yielding 19.03 g (95%) of product, mp 58°–60° C.

Step B: Preparation of 4-tetrahydropyranyloxy-4,5,6,7-tetrahydrobenzo[b]thiophene A mixture of 19.0 g (0.123 mol) of product from Step A, 15.53 g (0.185 mol) of dihydropyran, 2.56 g (0.010 mol) of pyridinium-4-toluenesulfonate, and 700 ml CH₂Cl₂ was stirred at ambient temperature for 5 hours. The reaction mixture was washed twice with half saturated NaCl solution, dried (Na₂SO₄), filtered, and evaporated. The residual colorless oil was distilled (112° C., 0.05 mm Hg) yielding a quantitative amount of product.

Step C: Preparation of 4-tetrahydropyranyloxy-4,5,6,7-tetrahydrobenzo[b]thiophene-2-sulfonamide To a solution of 11.17 g (0.047 mol) of product from Step B in 50 ml sieve-dried THF at −60° C. was added 33 ml (0.053 mol) of a 1.6M solution of n-butyl lithium in hexanes. After 1.5 hour, SO₂ was passed over the surface for 40 minutes. After an additional 50 minutes, ether was added and the cooling bath removed. After 30 minutes the resulting solids were collected by filtration. The filtrate was stored in the freezer overnight resulting in more solids. The combined yield of the intermediate sulfonate was 5.57 g (0.018 mol). The sulfinate was suspended in 35 ml CH₂Cl₂ and 2.68 g (0.020 mol) N-chlorosuccinimide was added at 0° C. After 2 hours the succinimide byproduct was removed by filtration. The filtrate was concentrated under reduced pressure yielding 4.79 g (0.014 mol) of the sulfonyl chloride whose existence was confirmed by NMR. This material was dissolved in 26 ml acetone and 13 ml concentrated NH₄OH was added at 0° C. After 15 minutes the ice bath was removed and after an additional 30 minutes the solvents were removed under reduced pressure. After 2 hours under high vacuum the yield of product was 5.96 g (40%).

Step D: Preparation of 4-hydroxy-4,5,6,7-tetrahydrobenzo[b]-thiophene-2-sulfonamide To a solution of thoroughly dried product from Step C (5.9 g, 0.98 mol) in 140 ml absolute ethanol (warming necessary to promote solubility) was added 467 mg (0.0018 mol) pyridinium 4-toluenesulfonate (PPTS). After stirring under N₂ at 55° C. for 3 hours, no reaction was detected by TLC. The solvent was removed under reduced pressure. Then, 125 ml absolute ethanol was added and PPTS was added until pH 3 was achieved. After 4 hours under N₂ at 55° C. the solvent was removed under reduced pressure. The residue was chromatographed on silica gel first with 85:15 CHCl₃:CH₃OH (v:v) and a second time with 90:10 CHCl₃:CH₃OH (v:v) saturated with NH₃. The product was recrystallized from H₂O after decolorizing with charcoal, yielding 700 mg (17%) of product mp 102°–103° C.

EXAMPLE 21

5-Oxo-4,5,6,7-tetrahydrobenzo[b]thiophene-2-sulfonamide

Step A: Preparation of 5-oxo-4,5,6,7-tetrahydrobenzo[b]thiophene ethylene ketal

A mixture of 5-oxo-4,5,6,7-tetrahydrobenzo[b]thiophene (25.3 g, 0.166 mole), p-toluenesulfonic acid monohydrate (2.5 g, 0.013 mole), ethylene glycol (50 ml) and toluene (400 ml) was stirred at reflux under a Dean-Stark trap for 3 hours. The toluene layer was separated from the cooled mixture. The ethylene glycol layer was diluted with water and extracted with toluene (3×100 ml). The combined toluene phases were washed with saturated Na₂CO₃ solution, water, and saturated NaCl solution. Toluene was stripped in vacuo, from the dried (anhydr. Na₂SO₄) and filtered extract, leaving 32.2 g of brown oil. Short path distillation gave 24.9 g (76%) of product as a colorless oil, b.p. 87°–91° C./0.1 mm that was characterized by nmr.

Step B: Preparation of 5-oxo-4,5,6,7-tetrahydrobenzo[b]thiophene-2-sulfonamide ethylene ketal Under N₂, a solution of the product from Step A (24.9 g, 0.127 mole) in dry, peroxide-free THF (130 ml) was stirred and cooled to −70° C. n-Butyllithium (87.5 ml of 1.6M solution in hexane) was added dropwise over 45 minutes. The resulting red solution was stirred at −70° C. for 30 minutes and then SO₂ was passed over the surface for 40 minutes. After the thick suspension was stirred at ambient temperature for another 30 minutes, it was diluted with ether (200 ml). The solid lithium sulfinate derivative was collected, washed with ether and dried in vacuo at room temperature. This solid (34.3 g) was suspended in dry CH₂Cl₂ (325 ml) and cooled to 5°–10° C. A solution of N-chlorosuccinimide (17.7 g, 0.133 mole) in CH₂Cl₂ (300 ml) was added dropwise over 30 min. Stirring was continued for 1.25 hours in the cold and then for 3 hours at room temperature. The gelatinous precipitate was removed by filtration through filter aid and solvent was stripped from the filtrate in vacuo. The residual brown oily sulfonyl chloride (30.4 g) was dissolved in acetone (300 ml) and cooled in an ice bath. Concentrated NH₄OH (100 ml) was added rapidly dropwise. After several hours at ambient temperature, the mixture was concentrated in vacuo and the residue was partitioned between water and ethyl acetate. The washed and dried ethyl acetate extract was concentrated in vacuo to a total volume of about 100 ml when the residue was thick with solid. The solid was collected, washed with cold ethyl acetate and dried to yield 12.6 g (36%) of product; m.p. 178°–180° C. An analytical sample after recrystallization from ethyl acetate had m.p. 180°–181° C.

Step C: Preparation of 5-oxo-4,5,6,7-tetrahydrobenzo[b]thiophene-2-sulfonamide

A solution of product from Step B (11.0 g, 0.04 mole) and p-toluenesulfonic acid monohydrate (1.0 g, 0.005 mole) in acetone (250 ml) was stirred at room temperature overnight and then at reflux for 4 hours. Acetone was stripped in vacuo and the residue was partitioned between ethyl acetate and saturated NaHCO₃ solution. The washed and dried ethyl acetate extract was concentrated in vacuo and the residual oily solid was triturated with cold ethyl acetate. The solid was collected to recover 5.14 g of starting material, m.p. 170°–176° C. The filtrate was evaporated in vacuo and the residual 4.7 g of crude, oily product was chromatographed on silica gel (500 g). Elution with 90 CHCl₃: 10 CH₃OH:1-H₂O (v/v/v) gave a pale yellow crystalline solid that was recrystallized from ethyl acetate to yield 1.65 g of product, m.p. 148°–150° C.

EXAMPLE 22

5-Hydroxy-4,5,6,7-tetrahydrobenzo[b]thiophene-2-sulfonamide

To a suspension of 5-oxo-4,5,6,7-tetrahydrobenzo[b]thiophene-2-sulfonamide (1.0 g, 0.0043 mole) in ethanol (30 ml) was added sodium borohydride (160 mg, 0.004 mole). The suspended solid dissolved within 10 minutes in a slightly exothermic reaction. Stirring was continued overnight at room temperature. After dilution with water (15 ml), the ethanol was stripped in vacuo. The residual aqueous solution was cooled in an ice bath and acidified with 6N HCl. The precipitate was collected, washed with water, and dried to yield 0.7 g (70%) of product as an off-white crystalline solid, mp 176°–179° C.

EXAMPLE 23

5,6-Dihydro-4-acetamido-4H-thieno[2,3-b]thiopyran-2-sulfonamide-7,7-dioxide

To a cooled solution of 96.6% H₂SO₄ (32 ml) was added dropwise with stirring a solution of 5,6-dihydro-4H-4-hydroxythieno[2,3-b]thiopyran-2-sulfonamide-7,7-dioxide (8.8 g, 0.031 mole) in CH₃CN (110 ml). After the addition, the mixture was stirred at room temperature overnight, then poured onto ice (600 g) and stirred for 1 hour. The suspension was filtered and the solid dried to yield 4.8 g of crude product. The filtrate was extracted with ethyl acetate (3X). The combined organic extracts were washed with saturated NaHCO₃ solution, dried, filtered and concentrated to dryness to yield 1.2 g of crude product (59%). An analytical sample was prepared by crystallization from CH₃OH; m.p. 263°–265° C.

EXAMPLE 24

5,6-Dihydro-4-aminothieno[2,3-b]thiopyran-2-sulfonamide-7,7-dioxide hydrochloride A mixture of 5,6-dihydro-4-acetamido-4H-thieno[2,3-b]thiopyran-2-sulfonamide-7,7-dioxide, from Example 23, (2.0 g, 0.0062 mol) in CH₃OH (20 ml) and 12N HCl (20 ml) was heated at reflux. After 6 hours, the solution was concentrated to dryness and the residue was treated with absolute ethanol. The mixture was concentrated to dryness and this procedure was repeated 4X. The final ethanol treatment was stirred, allowed to stand in the freezer overnight and filtered to yield 1.55 g (79%) of product; m.p. 251°–253° C.

EXAMPLE 25

5,6-Dihydro-4-(N-ethylamino)thieno[2,3-b]thiopyran-2-sulfonamide-7,7-dioxide

Under N₂, a suspension of 5,6-dihydro-4-acetamido-4H-thieno[2,3-b]thiopyran-2-sulfonamide-7,7-dioxide, from Example 23, (4,4 g, 0.14 mol) in THF (80 ml) was heated at reflux while a solution of borane-dimethylsulfide complex (BH₃.(CH₃)₂S) (4 ml of 10M) was added dropwise with stirring. After an additional 30 minutes at reflux, the suspension was concentrated to dryness and the residue was treated carefully with 6N HCl (28 ml). After the addition was complete, the solution was concentrated to dryness and the residue flushed dry 4X with absolute ethanol. The residue was treated with NaHCO₃ to pH 8.5 and the suspension was extracted with ethyl acetate (3X). The organic extracts were dried, filtered and concentrated to dryness. The residue was dry packed on silica gel and chromatographed on silica gel eluting with 10% CH₃OH-CHCl₃ (v:v) saturated with NH₃ to yield 3.0 g of product (71%); m.p. 161°–163° C. ((C₂H₅)₂O-CH₃OH).

EXAMPLE 26

5,6-Dihydro-4-formamido-4H-thieno[2,3-b]thiopyran-2-sulfonamide-7,7-dioxide and 6H-Thieno[2,3-b]thiopyran-2-sulfonamide-7,7-dioxide Under N₂, 95% H₂SO₄ (50 ml) was added dropwise with stirring to a cooled suspension of 5,6-dihydro-4H-4-hydroxythieno[2,3-b]thiopyran-2-sulfonamide-7,7-dioxide (10 g, 0.035 mol), KCN (20 g, 0.31 mol) in CF₃CO₂H (180 ml). After the addition, the mixture was heated at 60° C. overnight and then the CF₃CO₂H was removed under reduced pressure. The residue was poured carefully into saturated Na₂CO₃ solution, the pH was adjusted to 9.0 and the solution extracted with ethyl acetate (5X). The organic extracts were washed with saturated NaCl, dried, filtered and concentrated to dryness. The residue was dry packed on silica gel and chromatographed on silica gel eluting with 10% CH₃OH-CHCl₃ to yield 3.7 g of 6H-thieno[2,3-b]thiopyran-2-sulfonamide-7,7-dioxide, m.p. 214.5°–216.5° C. (40%) and then 4.1 g of 4,5-dihydro-4-formamido-4H-thieno[2,3-b]thiopyran-2-sulfonamide-7,7-dioxide (38%). An analytical sample of the latter was prepared by crystallization from CH₃OH-CH₃CN; m.p. 210°–212° C.

EXAMPLE 27

5,6-dihydro-4H-thieno[2,3-b]thiopyran-2-sulfonamide-7,7-dioxide-4-oxime

To a solution of 5,6-dihydro-4H-4-oxothieno[2,3-b]thiopyran-2-sulfonamide-7,7-dioxide (from Example 6) (5.0 g, 17.8 mmol) in ethanol (59 ml) was added to a solution of hydroxylamine hydrochloride (3.0 g, 42.7 mmol) in 2:1 (v:v) water-ethanol (15 ml). Sodium acetate.3H$_2$O (5.8 g, 42.7 mmol) in 2:1 (v:v) water-ethanol (15 ml) was added and the solution was heated at reflux for 1 hour and then stirred at room temperature overnight. The reaction mixture was concentrated to dryness, water added and solid product (5.3 g, 100%) collected and dried. The analytical sample was prepared by recrystallization from acetonitrile; m.p. 232°–234° C.

EXAMPLE 28

5,6-dihydro-4H-thieno[2,3-b]thiopyran-2-sulfonamide-7,7-dioxide-4-methoxime

To a solution of 5,6-dihydro-4H-4-oxothieno[2,3-b]thiopyran-2-sulfonamide-7,7-dioxide (from Example 6) (1.0 g, 3.6 mml) in ethanol (12 ml) was added a solution of methoxyamine hydrochloride (0.7 g, 8.6 mmol) in 2:1 (v:v) water-ethanol (3 ml). Sodium acetate 0.3H$_2$O (1.2 g, 8.6 mmol) in 2:1 (v:v) water-ethanol (3 ml) was and the solution was heated at reflux for 1 hour and then stirred at room temperature overnight. The reaction mixture was concentrated to dryness, water added and solid product (1.1 g, 100%) was collected and dried. An analytical sample was prepared by recrystallization from acetonitrile; m.p. 187°–189° C.

EXAMPLE 29

6,7-Dihydro-5H-7-oxofurano]3,2-b]thiopyran-2-sulfonamide

Step A: Ethyl 3-(3-Furylthio)propionate

A solution of 3-bromofuran (2.00 g, 0.014 mole) in ether (5 ml) was added over 15 minutes to a stirred solution of 1.6M n-butyllithium in hexane (10 ml, 0.016 mole) at −70° C. under a nitrogen atmosphere. The mixture was stirred for an additional 10 minutes and then sulfur (0.51 g, 0.016 mole) was added portionwise over 5 minutes. The mixture was stirred at −70° C. for 30 minutes, then allowed to warm to −15° C. when a solution of ethyl 3-bromopropionate (2.53 g, 0.014 m) in ether (10 ml) was added over 15 minutes while maintaining the temperature below 0° C. The mixture was stirred at 0° C. for 1 hour and then for 0.5 hour at ambient temperature. Water (50 ml) was added, followed by ether (50 ml), the layers were separated and the aqueous layer was extracted with ether (2×75 ml). The combined ether layers were washed with water, dried over sodium sulfate, and concentrated in vacuo to give 2.51 g of crude product.

The product was purified by chromatography on silica gel, eluting with methylene chloride, to give 0.57 g (20%) of pure product.

Step B: Preparation of 3-(3-Furylthio)propionic Acid

A mixture of ethyl 3-(3-furylthio)propionate (0.52 g, 0.0026 mole) and potassium hydroxide (0.29 g, 0.0052 m) in ethanol (25 ml) and water (1.0 ml) was stirred at ambient temperature for 4 hours. The mixture was concentrated in vacuo below 40° C., water (20 ml) was added to the residue and the solution extracted with methylene chloride (20 ml). The aqueous layer was acidified with 3NHCl, extracted with methylene chloride (3×25 ml) and the combined extracts washed twice with water. After drying over sodium sulfate, the solvent was evaporated in vacuo to give 0.15 g (33%) of oily product.

Step C: Preparation of 6,7-Dihydro-5H-furano[3,2-b]thiopyran-7-one

A mixture of 3-(3-furylthio)propionic acid (4.3 g, 0.025 mol), SUPER CEL® (5 g), and P$_2$O$_5$ (8 g) in toluene (80 ml) was mechanically stirred under N$_2$ at 100° C. After 2 hours, additional P$_2$O$_5$ (8 g) was added and the mixture heated for 3 hours at 100° C. The mixture was filtered, and the solid was washed with hot toluene (3X), and the filtrate concentrated to dryness to yield the product.

Step D: Preparation of 6,7-Dihydro-5H-furano[3,2-b]thiopyran-7-one-2-sulfonamide Employing the procedure substantially as described in Example 1, Step B but using as starting material the furan compound produced in Step C of this Example 29, there is produced the title compound.

EXAMPLE 30

6,7-Dihydro-5H-7-hydroxyfurano[3,2-b]thiopyran-2-sulfonamide

The procedure utilized to prepare 5,6-dihydro-4H-4-hydroxythieno[2,3-b]thiopyran-2-sulfonamide (Example 4) is used to prepare this product.

EXAMPLE 31

5,6-Dihydro-7H-7-hydroxyfurano[3,2-b]thiopyran-2-sulfonamide-4,4-dioxide

The procedure utilized to prepare 5,6-dihydro-4H-4-hydroxythieno[2,3-b]thiopyran-2-sulfonamide-7,7-dioxide (Example 18, Step C) is used to prepare the product.

Employing procedures substantially as described in the Examples cited below but starting with an N-(C$_{1-3}$alkyl)pyrrole or an N-benzyl pyrrole analog of the thiophene starting materials used in the cited examples there are prepared the corresponding pyrrolo[3,2-b]thiopyrans as follows:

| Example 29, Step C and D: | 6,7-Dihydro-5H—1-methyl-7-oxopyrrolo[3,2-b]thiopyran-2-sulfonamide<br>1-Benzyl-6,7-Dihydro-5H—7-oxo-pyrrolo[3,2-b]thiopyran-2-sulfonamide |
|---|---|
| Example 30 | 6,7-Dihydro-5H—7-hydroxy-1-methylpyrrolo[3,2-b]thiopyran-2-sulfonamide<br>6,7-dihydro-5H—7-hydroxy-pyrrolo[3,2-b]thiopyran-2-sulfonamide |
| Example 31 | 6,7-Dihydro-5H—1-methyl-7-oxopyrrolo[3,2-b]thiopyran-2-sulfonamide-4,4-dioxide;<br>1-Benzyl-6,7-Dihydro-5H—7-oxopyrrolo[3,2-b]thiopyran-2-sulfonomide-4,4-dioxide;<br>6,7-dihydro-5H—7-hydroxy-1-methylpyrrolo[3,2-b]thio-pyran-2-sulfonomide-4,4-dioxide; and<br>6,7-dihydro-5H—7-hydroxypyrrolo[3,2-b]thiopyran-2- |

-continued sulfonomide-4,4-dioxide

EXAMPLE 32

5,6-Dihydro-4H-4-hydroxythieno[2,3-b]thiopyran-2-sulfonamide-7,7-Dioxide

Step A: Preparation of 3-(2-thienylthio)propionic acid n-Butyl lithium (180 g, 2.81 mol) in hexane (1.6M solution) was added to a solution of thiophene (200 ml, 2.5 mol) in 1500 ml ether under $N_2$ while keeping the temperature between 25°-30° C. The mixture was stirred at room temperature for 1 hour then heated at reflux for 2 hours, cooled to −60° C. and sulfur (80.15 g, 2.5 mol) added. The mixture was stirred at −60° to −70° C. for 45 minutes, allowed to warm to −10° C. then cooled to −20° C. and $H_2O$ (500 ml) added slowly. The layers were separated and the aqueous layer added to a solution of 3-bromopropionic acid (382.5 g, 2.5 mol) in 250 ml $H_2O$ which was neutralized by the addition of $K_2CO_3$ (172.8 g, 1.25 mol) prior to the addition of the thiophenethiol. The organic layer was washed with $H_2O$ (500 ml and 100 ml) and the aqueous washes were added to the solution of the 3-bromopropionic acid (slight exotherm). The reaction mixture was stirred at room temperature for 18 hours then heated on the steam bath for 1 hour. After cooling to room temperature the mixture was extracted with ether (2×250 ml), cooled in an ice bath and acidified to pH 1.0 with 6NHCl. The acidified, aqueous mixture was extracted with ether (500 ml then 2×375 ml). The ether extracts were combined, washed with $H_2O$ (2×250 ml) and dried over $Na_2SO_4$. Evaporation of the solvent yielded 410.2 g of crude product, which was distilled in vacuo. The fraction boiling at 154°-164° C. at 0.9 mm Hg was collected yielding 346.8 g (73.7%) of product.

Step B: Preparation of 5,6-Dihydro-4H-4-oxothieno[2,3-b]thiopyran

A mixture of 3-(2-thienylthio)propionic acid (65 g, 0.346 mol), SUPER CEL ® (65 g), toluene (1 l) and $P_2O_5$ (100 g, 0.7 mol) was heated on a steam bath with mechanical stirring under $N_2$ in a resin flask. After 3 hours, $P_2O_5$ (100 g, 0.7 mol) was added and the mixture heated for 2 hours. The thick purple suspension was then filtered through a SUPER CEL ® pad, washed with hot toluene (1 l). The organic extracts were washed with 5% NaOH, dried, filtered and concentrated to dryness to yield 37.7 g (69%) of product.

Step C: Preparation of 5,6-Dihydro-4H-4-oxothieno[2,3-b]thiopyran-2-sulfonic acid To a stirred solution of 5,6-dihydro-4-oxothieno[2,3-b]thiopyran (85.1 g, 0.50 mol) in methylene chloride (800 ml) at −10° C. was added in one portion acetic anhydride (143.8 ml, 1.5 mol) followed by concentrated sulfuric acid (30.7 ml, 0.55 mol) added dropwise over 10 minutes. The mixture was stirred at 10° to 15° C. for ½ hour and filtered. The olive green, hygroscopic solid was washed with ether and was immediately dried in vacuo. The weight of sulfonic acid obtained was 120.9 g, (96.6% of crude product).

Step D: Preparation of 5,6-Dihydro-4H-4-oxothieno[2,3-b]thiopyran-2-sulfonyl chloride A suspension of 5,6-dihydro-4-oxothieno[2,3-b]thiopyran-2-sulfonic acid (120.9 g, 0.483 mol) in methylene chloride (800 ml) was stirred at 0° C. as phosphorus pentachloride (140.8 g, 0.676 mol) was added in one portion. The cooling bath was removed and the mixture was stirred for 1½ hours as the temperature rose to room temperature. The resulting dark maroon solution was added to 400 ml of ice and water. The methylene chloride layer was separated and the aqueous layer was extracted with methylene chloride (3×50 ml). The combined methylene chloride solutions were washed with saturated NaCl solution and filtered through activated carbon. The amber filtrate was dried over anhydrous $Na_2SO_4$, filtered and concentrated in vacuo at room temperature. The sulfonyl chloride was obtained as a pale grayish-green solid (129 g), (yield nearly quantitative).

Step E: Preparation of 5,6-Dihydro-4H-4-oxothieno[2,3-b]thiopyran-2-sulfonamide

The crude 5,6-dihydro-4H-4-oxothieno[2,3-b]thiopyran-2-sulfonyl chloride (129 g, 0.48 mol) was dissolved in acetone (400 ml) with warming and was added to concentrated $NH_4OH$ at −30° C. with rapid stirring over a 20 minute period. The mixture was stirred at 0° C. for an additional ¼ hour and concentrated in vacuo at room temperature to remove the acetone. The yellow suspension remaining was filtered and the solid was washed with cold water. Then it was dried in the steam cabinet over night. The sulfonamide (99 g) showed several minor impurities by TLC. The yield was 80% of material melting at 208°-213° C. Recrystallization from $CH_3OH/CH_3CN$, gave material with m.p. 216°-218° C. (66% recovery).

The mother liquors from the above material were combined and the solute therefrom was chromatographed on silica gel by elution with ethyl acetatehexanes. The fractions containing the major component were combined and yielded 33.2 g of 4-chloro-6H-thieno[2,3-b]thiophene-2-sulfonamide, m.p. 158°-160° C.

Step F: Preparation of 5,6-Dihydro-4H-4-hydroxythieno[2,3-b]thiopyran-2-sulfonamide To a mixture of 5,6-Dihydro-4H-4-oxothieno[2,3-b]thiopyran-2-sulfonamide (50 g, 0.2 mol) in absolute ethanol (2 l) was added with stirring $NaBH_4$ (10 g, 0.26 mol) and the mixture heated at reflux. After 20 minutes, the suspension was cooled, and the pH adjusted to 8.5. The ethanol was removed in vacuo and the solid removed by filtration, washed with $H_2O$ and dried to yield 51 g of product. The aqueous layer was extracted with ethyl acetate (2×). The organic extracts were dried, filtered and concentrated to dryness to yield 14 g of product. The combined solids (65 g) were recrystallized from $CH_3OH$-$CH_3CN$ to yield 47.9 g (95%) of product; m.p. 166°-167° C.

Step G: Preparation of 5,6-Dihydro-4H-4-hydroxythieno[2,3-b]thiopyran-2-sulfonamide-7,7-dioxide To a suspension of 5,6-Dihydro-4H-4-hydroxy-thieno[2,3-b]thiopyran-2-sulfonamide (50 g, 0.199 mol) in $CH_3OH$ (650 ml) was added dropwise a solution of OXONE® (184 g, 0.3 mol) in $H_2O$ (1 l). After a slight exotherm (25° to 45° C.), the reaction was stirred at room temperature for 3 hours and then the $CH_2OH$ was removed in vacuo. The aqueous layer was extracted with ethyl acetate (6X). The organic extracts were dried, filtered, concentrated to dryness. The residue was triturated with ether, and filtered to yield 47.3 g (84%) of product; m.p. 169°–171° C.

EXAMPLE 33

5,6-Dihydro-4H-4-(N-methylamino)thieno[2,3-b]thio-pyran-2-sulfonamide-7,7-dioxide hydrochloride To a solution of 5,6-dihydro-4H-4-formamido-thieno[2,3-b]thiopyran-2-sulfonamide-7,7-dioxide (2.3 g, 0.0074 mol) in THF (60 ml) heated at reflux there was added dropwise from a syringe borane dimethylsulfide (2.3 ml, 10M, 0.023 mol). After heating at a gentle reflux for 2 hours while collecting the distilled dimethyl sulfide, the suspension was treated with 6N HCl (20 ml) and heated at reflux for an additional 1 hour. The suspension was then concentrated to dryness, flushed with ethanol (4x), crystallized from $CH_3OH$ after filtering the solution through a pad of filter aid and decolorizing carbon to yield 1.8 g of product (75%); m.p. 275°–276° C. (dec).

EXAMPLE 34

5,6-Dihydro-4H-4-(N,N-dimethylamino)thieno[2,3-b]thiopyran-2-sulfonamide-7,7-dioxide hydrochloride A solution of 5,6-dihydro-4H-4-aminothieno[2,3-b]thiopyran-2-sulfonamide-7,7-dioxide hydrochloride (5 g, 0.016 mol), 88% formic acid (40 ml), 37% formalin (25 ml) and $H_2O$ (16 ml) was heated at 100° C. After 15 hours, the solution was concentrated to dryness and flushed with ethanol (4x). The residue was treated with a saturated $NaHCO_3$ solution and extracted with ethyl acetate (4x). The organic layer was dried, filtered and concentrated to dryness. The residue was dry packed on silica gel (600 ml) and chromatographed on silica gel eluting with 5–10% $CH_3OH-CHCl_3$ to yield 1.8 g of crude amine. An analytical sample was prepared from ethanolic HCl and crystallized from $CH_3OH$ to yield 1.8 g of product (33%); m.p. 252°–254° C. (dec).

EXAMPLE 35

5,6-Dihydro-4H-4-chlorothieno[2,3-b]thiopyran-2-sulfonamide-7,7-dioxide

To a solution of 5,6-dihydro-4H-4-hydroxy-thieno[2,3-b]thiopyran-2-sulonamide-7,7-dioxide (8.0 g, 0.028 mol) in $CH_3CN$ (300 ml) and triphenylphosphine (14.8 g, 0.056 mol) was added $CCl_4$ (12 ml, 0.12 mol). After stirring overnight at room temperature triphenyl-phosphine (7.5 g, 0.028 mol) and $CCl_4$ (5 ml) was added and the mixture heated at 50° C. After 2 hours, silica gel (400 ml) was added. The mixture concentrated to dryness and the residue placed on a column of silica gel. The product was eluted with 2.5% $CH_3OH-CHCl_3$ to yield 4.6 g (55%) of the title compound; m.p. 167°–169° C.

EXAMPLE 36

5,6-Dihydro-5,5-dimethyl-4H-thieno[2,3-b]thiopyran-4-one-2-sulfonamide

Step A: Preparation of 2,2-Dimethyl-3-(2-thienylthio)propanoic Acid

A solution of thiophene (30.79 g, 0.366 m) in ether (220 ml) was stirred in a nitrogen atmosphere while 1.6M n-butyl lithium in hexane (2.57 ml, 0.41 m) was added over 35 minutes, maintaining the temperature at 25°–30° C. The mixture was stirred at ambient temperature for 1 hour, then refluxed for 2 hours. After cooling to −70° C., sulfur (11.73 g, 0.366 m) was added over five minutes. The mixture was stirred at −60° C. to −70° C. for 45 minutes, allowed to warm to −20° C. over 30 minutes, and water (75 ml) was added dropwise. The layers were separated and the aqueous layer was added to a solution of β-chloropivalic acid (50.00 g, 0.366 m) in potassium carbonate (25.29 g, 0.183 m) dissolved in water (70 ml). The ether layer was washed with 75 ml and 25 ml of water and the washings were added to the pivalic acid solution and stirred at ambient temperature under nitrogen for about 17 hours. The mixture was heated on a steam bath for 1 hour, cooled and washed with ether (2×75 ml). The aqueous solution was acidified with 6N hydrochloric acid and extracted with ether (3×100 ml). After washing with water and drying over sodium sulfate, the solvent was evaporated in vacuo. The residue was distilled to give 59.13 g (75%) of product boiling at 145°–151° C./0.5 mm Hg.

Step B: Preparation of 5,6-Dihydro-5,5-dimethyl-4H-thieno[2,3-b]thiopyran-4-one A mixture of 2,2-dimethyl-3-(2-thienylthio)propanoic acid (53.65 g, 0.25 m), diatomaceous earth (54 g) and phosphorus pentoxide (87 g) in toluene (870 ml) was vigorously stirred and heated at 100° C. After 2 hours, additional phosphorous pentoxide (87 g) was added and the mixture was heated for 3 hours more. After filtering the hot mixture, the solid was washed with hot toluene (3×500 ml) and the combined filtrate and washings were concentrated under reduced pressure to afford 33.17 g (67%) of crude product. This material was combined with 2.89 g of crude product from a previous reaction and distilled to yield 25.07 g (46%) of pure product boiling at 96°–100° C./0.4 mm Hg.

Step C: Preparation of 5,6-Dihydro-5,5-dimethyl-4H-thieno[2,3-b]thiopyran-4-one-2-sulfonamide Acetic anhydride (30.63 g, 0.30 m) was added to a solution of 5,6-dihydro-5,5-dimethyl-4H-thieno[2,3-b]thiopyran-4-one (19.84 g, 0.10 m) in methylene chloride (160 ml) with stirring at −8° C. With continued ice-bath cooling, concentrated sulfuric acid (10.8 g, 0.11 m) was added dropwise over 10 minutes while maintaining the temperature below 10° C. The mixture was stirred at ambient temperature for 1.5 hours, then a solution of potassium acetate (10.8 g, 0.11 m) in 95% ethanol (65 ml) was added over 10 minutes with occasional cooling to keep the temperature at 20°–25° C. After stirring at ambient temperature for 1 hour, the solid was collected and dried. The product was stirred with a mixture of phosphorous pentachloride (25.0 g, 0.12 m) and 18-crown-6 (1.3 g) in acetonitrile (565 ml) at ambient temperature for 23.5 hours. The solvent was concentrated in vacuo, the residue was extracted with methylene chloride (500 ml), filtered and the filtrate was evaporated under reduced pressure. The oily residue was dissolved in acetone (350 ml), cooled in an ice bath and stirred while concentrated ammonium hydroxide (175 ml) was added over 15 minutes. After stirring at ambient temperature for 1 hour, the mixture was concentrated under reduced pressure. The residue was dissolved in 0.5M potassium hydroxide (800 ml), washed with methylene chloride (2×400 ml), acidified with 6N hydrochloric acid, and extracted with ethyl acetate (3×500 ml). After washing with water and drying over sodium sulfate, the solvent was evaporated in vacuo to give 24.60 g (89%) of crude product which was purified by chromatography on silica gel, eluting with 10% methanol-chloroform.

An analytical sample melted at 189°–190.5° C. after recrystallization from nitromethane.

EXAMPLE 37

5,6-Dihydro-4-hydroxy-5,5-dimethyl-4H-thieno[2,3-b]thiopyran-2-sulfonamide

A mixture of 5,6-dihydro-5,5-dimethyl-4H-thieno[2,3-b]thiopyran-4-one-2-sulfonamide (12.8 g, 0.046 m) and sodium borohydride (2.27 g, 0.060 m) in ethanol (460 ml) was stirred under reflux for 1 hour. After cooling to ambient temperature, the mixture was acidified by the rapid addition of 1N hydrochloric acid (65 ml), then rendered basic with saturated sodium bicarbonate solution and concentrated in vacuo to remove ethanol. The aqueous suspension was distributed between ethyl acetate (300 ml) and water (200 ml), the aqueous layer was separated and extracted with ethyl acetate (2×300 ml), the combined ethyl acetate layers were washed with saturated sodium bicarbonate solution, twice with water and dried over sodium sulfate. The solvent was evaporated under reduced pressure to yield 11.71 g (91%) of product. An analytical sample melted at 158°–159° C. after recrystallization from nitromethane.

EXAMPLE 38

5,6-Dihydro-4-hydroxy-5,5-dimethyl-4H-thieno[2,3-b]thiopyran-2-sulfonamide-7,7-dioxide A solution of OXONE ® (2.71 g, 0.0044 m) in water (15 ml) was added to a solution of 5,6-dihydro-4-hydroxy-5,5-dimethyl-4H-thieno[2,3-b]thiopyran-2-sulfonamide (0.90 g, 0.0032 m) in methanol (15 ml) over 10 minutes and the mixture was stirred at ambient temperature for 2.5 hours. The mixture was filtered, the solid was washed with methanol, and the combined filtrate and washings were concentrated in vacuo below 65° C. to remove methanol. The aqueous suspension was extracted with ethyl acetate (3×50 ml), the combined extracts were washed with water, dried over sodium sulfate and evaporated under reduced pressure to give 0.91 g (91%) of crude product which was purified by chromatography on silica gel, eluting with 10% methanol-chloroform.

An analytical sample melted at 172°–173.5° C. after recrystallization from water.

EXAMPLE 9

5,6-Dihydro-5,5-dimethyl-4H-thieno[2,3-b]thiopyran-4-one-2-sulfonamide-7,7-dioxide A solution of Jones reagent was prepared by dissolving 26.72 g of chromic trioxide in 23 ml of concentrated sulfuric acid and diluting with water to a volume of 100 ml. To a solution of 5,6-dihydro-4-hydroxy-5,5-dimethyl-4H-thieno[2,3-b]thiopyran-2-sulfonamide-7,7-dioxide (3.00 g, 0.0096 m) in acetone (85 ml) was added 4.5 ml of the Jones reagent solution over 5 minutes at ambient temperature. After stirring for an additional 10 minutes, the mixture was poured into water (300 ml), and the combined extracts were washed with water, saturated sodium bicarbonate solution, and twice more with water. After drying over sodium sulfate, the solvent was evaporated under reduced pressure to yield 2.89 g (97%) of product. An analytical sample melted at 190°–191.5° C. after recrystallization from nitromethane.

EXAMPLE 40

6H-Thieno[2,3-b]thiopyran-2-sulfonamide-7,7-dioxide

A mixture of 5,6-dihydro-4-hydroxy-4H-thieno[2,3-b]thiopyran-2-sulfonamide-7,7-dioxide (0.90 g, 0.0031 m), concentrated sulfuric acid (3 ml), and trifluoroacetic acid (20 ml) was stirred and heated at 50° C. for 20.5 hours. After removal of trifluoroacetic acid under reduced pressure, the residue was dissolved in ethyl acetate (25 ml) and the solution was washed with water, twice with saturated sodium bicarbonate solution, twice more with water and dried over sodium sulfate. The solvent was concentrated in vacuo to yield 0.74 g (90%) of crude product. The product was purified by recrystallization from nitromethane after treatment with decolorizing carbon. An analytical sample melted at 214.5°–216° C. (See Example 26).

EXAMPLE 41

5,6-Dihydro-4-(N-tert-butoxycarbonylglycycloxy)-4H-thieno[2,3-b]thiopyran-2-sulfonamide-7,7-dioxide Commercial N-tert-butoxycarbonyl-glycine (3.68 g, 0.021 mole) and 5,6-dihydro-4H-4-hydroxythieno[2,3-b]thiopyran-2-sulfonamide-7,7-dioxide (5.6 g, 0.02 mole) were dissolved in 100 ml of dry tetrahydrofuran. The acylation catalyst 4-dimethylaminopyridine (0.24 g, 0.002 mole) was added and the mixture was cooled to 0° C. (under nitrogen). To this was added dropwise (20 minutes) a solution of 4.2 g (0.021 mole) of dicyclohexylcarbodiimide in 20 ml of tetrahydrofuran. Stirring was continued for 1 hour in an ice bath and then at room temperature overnight. The solid which formed (4.75 g) was removed and the filtrate was concentrated to 11.5 g of gum. This was triturated with hexane and dried to give 10.23 g of off-white powdery solid. This was chromatographed over 550 g of silica gel 60 using CHCl$_3$/MeOH: 85/15 to give 5.03 g (57%) of product, m.p. 95°–110° C.

Employing the procedure substantially as described in Example 41 but using as starting material N-tert-butoxycarbonyl-4-aminobutyric acid there was prepared 5,6-dihydro-4-(N-tert-butoxycarbonyl-4-aminobutyryloxy)-4H-thieno[2,3-b]thiopyran-2-sulfonamide-7,7-dioxide, m.p. 60°–70° C. (Softens).

EXAMPLE 42

5,6-Dihydro-4-glycyloxy-4H-thieno[2,3-b]thiopyran-2-sulfonamide-7,7-dioxide hydrochloride The tert-butoxycarbonylglycyloxy compound from Example 41 (4.4 g, 0.01 mole) was stirred with 150 ml of ethyl acetate, resulting in a slightly turbid solution. This was clarified by filtration to give 40 mg of insoluble material. Initially, one equivalent (2.08 ml) of 4.82N HCl/ethyl acetate was added. This gave no precipitate after 2 hours, so an extra amount (20.8 ml) was added and stirring continued overnight. A white solid was deposited on the sides of the flasks. This was collected and washed with ether to give 2.87 g of material. The entire amount was crystallized by dissolving it in 60 ml of methanol and adding 80 ml of ether, resulting in the deposition of 2.07 g (55%) of the product hydrochloride m.p. 238°–240° C.

Employing the procedure substantially as described in Example 42 but starting with the N-tert-butoxycarbonyl-4-aminobutyryloxy compound from Example 41 there was prepared 5,6-dihydro-4-(4-aminobutyryloxy)-4H-thieno[2,3-b]thiopyran-2-sulfonamide-7,7-dioxide hydrochloride, m.p. 204°–206° C.

EXAMPLE 43

5,6-Dihydro-4-(N-n-propylamino)-4H-thieno[2,3-b]thiopyran-2-sulfonamide-7,7-dioxide hydrochloride To a cooled suspension of 5,6-dihydro-4-hydroxy-4-H-thieno[2,3-b]thiopyran-2-sulfonamide-7,7-dioxide (4.4 g, 0.016 mol) in propionitrile (60 ml) was added dropwise at 0°–4° C. 96.6% $H_2SO_4$ (16 ml). After the addition, the solution was stirred overnight at room temperature. The solution was then poured into ice (500 g) and stirred at room temperature. After 2 hours, the suspension was extracted with ethyl acetate (4x) and the organic layer was washed with saturated $NaHCO_3$ until basic. The resulting organic extract was dried, filtered and concentrated to dryness. The residue was treated with THF (50 ml) and the solution heated at reflux while a solution of borane-dimethylsulfide complex ($BH_3\cdot(CH_3)_2S$) (3.5 ml of 10M solution) was added dropwise with stirring and the distilled dimethylsulfide and some THF in a short path distillation apparatus was collected. After an additional 30 minutes at reflux, the suspension was concentrated to dryness and the residue treated carefully with 6N HCl (24 ml). The mixture was heated at reflux for 10 minutes, and then concentrated to dryness. The residue was treated with saturated $NaHCO_3$ until basic (pH 8.5) and extracted with ethyl acetate (5x). The organic extracts were dried, filtered and concentrated to dryness. The residue was chromatographed on silica and eluted with 10% $CH_3OH$-$CHCl_3$ saturated with $NH_3$. The product was crystallized as the HCl salt from ethanolic HCl to yield 1.1 g (19%) of product, m.p. 272°–274° C.

EXAMPLE 44

5,6-Dihydro-4H-thieno[2,3-b]thiopyran-2-sulfonamide-7,7-dioxide

A solution of 6H-thieno[2,3-b]thiopyran-2-sulfonamide-7,7-dioxide (3.05 g, 0.011 m) is absolute ethanol (130 ml) and methanol (20 ml) was hydrogenated on a Parr apparatus at 40 psi with 5% palladium on carbon catalyst (250 mg) at ambient temperature. After 15 minutes, 10% palladium on carbon catalyst (350 mg) was added, followed by an identical addition after 30 minutes. After 16 hours, the catalyst was filtered and the filtrate was concentrated in vacuo. The residue was dissolved in absolute ethanol (100 ml) and methanol (50 ml) and hydrogenated at 50 psi with 10% palladium on carbon catalyst (500 mg) for 16 hours. The catalyst was filtered off and the filtrate was evaporated under reduced pressure. The solid residue was chromatographed on silica gel, eluting with 10% methanol-chloroform to give 2.33 g (76%) of product.

An analytical sample melted at 199.5°–200.5° C. after treatment with decolorizing carbon and crystallization from nitromethane.

EXAMPLE 45

5,6-Dihydro-4H-4-hydroxymethylthieno[2,3-b]thiopyran-2-sulfonamide-7,7-dioxide

Step A: Preparation of 5,6-Dihydro-4H-4-[2-(1,3-dithianylidene)]thieno[2,3-b]thiopyran To a cooled solution (0°–4° C.) of 2-trimethylsilyl-1,3-dithiane (19.2 g, 0.1 mol) in dry THF (100 ml) was added dropwise under $N_2$ a solution of 1.6M n-butyl lithium in hexane (62.5 ml, 0.1 mol). After the addition, the suspension was stirred for 15 minutes at 0° C. and then a solution of 5,6-dihydro-4H-4-oxothieno[2,3-b]thiopyran (17 g, 0.1 mol) in THF (50 ml) was added dropwise. After 15 minutes at 0° C., the mixture was stirred for 1 hour at room temperature and a saturated solution of NaCl was added. The mixture was extracted with ethyl acetate (3x) and the organic extracts were dried, filtered and concentrated to dryness. The residue was triturated with ligroin-ether, cooled and filtered to yield 14.65 g (54%) of product.

Step B: Preparation of 5,6-Dihydro-4H-thieno[2,3-b]thiopran-4-carboxylic acid To a solution of product from Step A (14.5 g, 0.053 mol) in 2.5N HCl-EtOH (250 ml) was bubbled in dry HCl gas while heating the solution to reflux. After purging for ½ hour, the solution was heated at reflux for 2 hours and then at 50° C. overnight. The mixture was concentrated to dryness, the residue treated with KOH (25 g, 0.45 mol) in 95% EtOH (150 ml) and the mixture heated at reflux with stirring for 5 hours. The mixture was then concentrated to dryness, $H_2O$ added, and extracted with ethyl acetate (3x) and the organic extract discarded. The aqueous layer was adjusted to pH 1 with 12N HCl and extracted with ethyl acetate (3x). The combined extract was dried, filtered and concentrated to dryness to yield 7.65 g (72%) of product.

Step C: Preparation of 5,6-Dihydro-4H-4-hydroxymethylthieno[2,3-b]thiopyran

To a suspension of lithium aluminum hydride (6.8 g, 0.18 mol) in THF (100 ml) was added dropwise under $N_2$ a solution of product from Step B (16.8 g, 0.084 mol) in THF (150 ml). After stirring for 2 hours at room temperature, the mixture was cooled in an ice bath and a saturated solution of $Na_2SO_4$ (200 ml) was carefully added dropwise with stirring. The suspension was then filtered through filter aid and the pad washed with THF and then $CHCl_3$. The organic solvents were evaporated from the filtrate and saturated $NaHCO_3$ added to the aqueous layer. The resulting aqueous layer was extracted with $CHCl_3$ (3x). The combined organic extracts were dried, filtered and concentrated to dryness to yield 13 g (83%) of product.

Step D: Preparation of 5,6-Dihydro-4H-4-(2-methoxyethoxymethoxy)methyl-thieno[2,3-b]thiopyran To a solution of product from Step C (13 g, 0.07 mol), diisopropylethylamine (13 g, 0.1 mol) in $CH_2Cl_2$ (200 ml) under $N_2$ was added dropwise 2-methoxyethoxymethylchloride (12.4 g, 0.1 mol) in $CH_2Cl_2$ (30 ml). After stirring at room temperature overnight, the solution was washed with cold 1N HCl (2x), saturated $NaHCO_3$ solution, dried, filtered and concentrated to dryness. The residue was chromatographed on silica gel and the product eluted with 20% ethyl acetate/hexanes to yield 14.2 g (67%) of product.

Step E: Preparation of 5,6-Dihydro-4H-4-(2-methoxyethoxymethoxy)methyl-thieno[2,3-b]thiopyran-2-sulfonamide To a flame dried flask under $N_2$ was added product from Step D (9.0 g, 0.033 mol) in dry THF (150 ml). The solution was cooled to $-10°$ to $-20°$ C. and a solution of 1.6M n-butyl lithium in hexane (30 ml, 0.048 mol) was added dropwise. After the addition, the suspension was stirred an additional 0.5 hour at $-10°$ to $-20°$ C. and then $SO_2$ gas was passed over the surface for 0.75 hour. After an additional 5 minutes at $-10°$ to $-20°$ C., ether (700 ml) was added and the suspension was stirred at room temperature for 1 hour and then concentrated to dryness. The residue was treated with cold $CH_2Cl_2$ (400 ml) and N-chlorosuccinimide (4.4 g, 0.33 mol) and the mixture was stirred at room temperature overnight. The mixture was filtered through filter aid and the filtrate concentrated to dryness. The residue was dissolved in acetone (50 ml) and added to concentrated aqueous $NH_3$ (50 ml). The acetone was removed under reduced pressure and the aqueous layer extracted with ethyl acetate (3x). The combined organic extracts were dried, filtered and concentrated to dryness. The residue was chromatographed on silica gel and the product eluted with 30% ethyl acetate-hexanes to yield 7.1 g (61%) of product.

Step F: Preparation of 5,6-Dihydro-4H-4-(2-methoxyethoxymethoxy)methyl-thieno[2,3-b]thiopyran-2-sulfonamide-7,7-dioxide To a solution of product from Step E (7.1 g, 0.02 mol) in $CH_3OH$ (65 ml) stirred at room temperature was added dropwise a solution of OXONE ® (18.4 g, 0.03 mol) in $H_2O$ (100 ml). The suspension was stirred at room temperature overnight and then filtered. The filter pad was washed well with $CH_3OH$ and the resulting filtrate was concentrated to remove the $CH_3OH$. The aqueous layer was extracted with ethyl acetate (3x). The combined organic layers were dried, filtered, and concentrated to dryness to yield 8.2 g (100%) of product.

Step G: Preparation of 5,6-Dihydro-4H-4-hydroxymethylthieno[2,3-b]thiopyran-2-sulfonamide-7,7-dioxide A solution of product from Step F (7.7 g, 0.02 mol) in $CH_3OH$ (100 ml) was added dropwise to a cooled solution of $H_2SO_4$ (100 ml) and $H_2O$ (100 ml). After the addition, the mixture was stirred an additional 0.5 hour at $0°-4°$ C. and then poured into $H_2O$. The aqueous layer was extracted with ethyl acetate (5x). The organic layers were dried, filtered and concentrated to dryness. The residue was dry packed on silica gel and placed on a column of silica gel. The product was eluted with ethyl acetate/hexane/$CH_3OH$ (20:10:1) to yield 2.45 g (41%) of product, m.p. 132°–134° C.

EXAMPLE 46

4-[(Aminocarbonyl)amino]-5,6-dihydro-4H-thieno[2,3-b]thiopyran-2-sulfonamide-7,7-dioxide To a solution of 4-amino-5,6-dihydro-4H-thieno[2,3-b]thiopyran-2-sulfonamide-7,7-dioxide (2.0 g, 0.0061 mol) in $H_2O$ (20 ml) was added portionwise potassium cyanate (3.0 g, 0.037 mol). The mixture was stirred overnight at room temperature then acidified to pH 2.0 and extracted with ethyl acetate (3x). The organic extracts were dried, filtered and concentrated to dryness. The residue was chromatographed on silica gel and the product eluted with 20% $CH_3OH$—$CHCl_3$ saturated with $NH_3$ gas to yield 1.3 g of crude product. Crystallization from $CH_3OH$—$CHCl_3$ gave 0.95 g (48%) of product, m.p. 242°–244° C.

EXAMPLE 47

4-(N,N-Diethylamino)-5,6-dihydro-4H-thieno[2,3-b]thiopyran-2-sulfonamide-7,7-dioxide

Step A: Preparation of 4-(N-Ethyl-N-acetylamino)-5,6-dihydro-4H-thieno[2,3-b]thiopyran-2-sulfonamide-7,7-dioxide To a mixture of 4-(N-ethylamino)-5,6-dihydro-4H-thieno[2,3-b]thiopyran-2-sulfonamide-7,7-dioxide (1.2 g, 0.0035 mol) in THF (30 ml) and triethylamine (1.1 ml, 0.79 g, 0.0078 mol) under $N_2$ was added dropwise at room temperature a solution of acetyl chloride (0.26 ml, 0.28 g, 0.0036 mol) in THF (15 ml). After 2 hours, the mixture was poured into a saturated solution of $NaHCO_3$ and extracted with ethyl acetate (3x). The organic extracts were dried, filtered and concentrated to dryness to yield 1.0 g (83%) of product.

Step B: Preparation of 4-(N,N-diethylamino)-5,6-dihydro-4H-thieno[2,3-b]thiopyran-2-sulfonamide-7,7-dioxide To a suspension of product from Step A (1.8 g, 0.005 mol) in THF (40 ml) heated at reflux under $N_2$ was added dropwise borane dimethylsulfide (10M, 1.5 ml, 0.015 mol) with the continuous removal of dimethylsulfide by way of a short path distillation apparatus. After 1 hour, the mixture was concentrated to dryness and the residue treated carefully with 6N HCl (12 ml). After heating at reflux for 0.5 hour, the mixture was concentrated to dryness. The residue was treated with $NaHCO_3$ and the suspension extracted with ethyl acetate (4x). The organic extracts were dried, filtered and concentrated to dryness. The residue was chromatographed on silica gel and the product eluted with 5% $CH_3OH$—$CHCl_3$ saturated with $NH_3$ gas. The product was crystallized as the hydrochloride salt from ethanol to yield 1.1 g of product (56%), m.p. 236°–238° C.

EXAMPLE 48

5,6-Dihydro-5-bromo-4-hydroxy-4H-thieno[2,3-b]thiopyran-2-sulfonamide-7,7-dioxide

Step A: Preparation of 5,6-Dihydro-5-bromo-4H-thieno[2,3-b]thiopyran-4-one-2-sulfonamide A solution of 5,6-dihydro-4H-thieno[2,3-b]thiopyran-4-one-2-sulfonamide (3.50 g, 0.014 m) in dry tetrahydrofuran (70 ml) was stirred at ambient temperature while a solution of pyridinium bromide perbromide (6.08 g, 0.019 m) in dry tetrahydrofuran (35 ml) and acetonitrile (10 ml) was added over 15 minutes. After stirring at ambient temperature for 1 hour, the reaction mixture was added to water (100 ml) and concentrated in vacuo to remove tetrahydrofuran and acetonitrile. The aqueous mixture was extracted with ethyl acetate (3×100 ml), the combined extracts were washed with water, dried over sodium sulfate and concentrated to dryness in vacuo. The residue was partially purified by chromatography on silica gel, eluting with 50% ethyl acetate-hexane, to yield 3.68 g (80%) of material which was used in the next reaction without further purification.

Step B: Preparation of 5,6-Dihydro-5-bromo-4-hydroxy-4H-thieno[2,3-b]thiopyran-2-sulfonamide A suspension of 5,6-dihydro-5-bromo-4H-thieno[2,3-b]thiopyran-4-one-2-sulfonamide (2.58 g, 0.0079 m) in methanol (100 ml) was cooled to $-10°$ C. and vigorously stirred while a solution of sodium borohydride (0.45 g, 0.012 m) in water (10 ml) was added over 25 minutes while maintaining the temperature at $-10°$ to $-5°$ C. The mixture was stirred at ambient temperature for 2 hours, then acidified with 6N hydrochloric acid and concentrated in vacuo below 40° C. The residue was distributed between ethyl acetate (100 ml) and water (100 ml), the aqueous layer was separated and again extracted with ethyl acetate (2×75 ml). The combined extracts were washed with water, dried over sodium sulfate and concentrated in vacuo to give 2.42 g (93%) of crude product. Partial purification was effected by chromatography on silica gel, eluting with 5% methanol-chloroform, to yield 1.71 g of product which was used in the subsequent step without further purification.

Step C: Preparation of 5,6-Dihydro-5-bromo-4-hydroxy-4H-thieno[2,3-b]thiopyran-2-sulfonamide-7,7-dioxide A suspension of 5,6-dihydro-5-bromo-4-hydroxy-4H-thieno[2,3-b]thiopyran-2-sulfonamide (0.59 g, 0.0018 m) in methanol (10 ml) was stirred while a solution of 'OXONE' (1.54 g, 0.0025 m) in water (10 ml) was added over 10 minutes. After stirring at ambient temperature for 2½ hours, an additional 0.75 g (0.0012 m) of 'OXONE' dissolved in water (5 ml) was added and the mixture was stirred for 16 hours more. The mixture was filtered and the filtrate was concentrated in vacuo below 60° C. to remove methanol. The resultant cloudy aqueous solution was extracted with ethyl acetate (3×50 ml), the combined extracts were washed with water, dried over sodium sulfate and evaporated in vacuo to yield 0.62 g of material which still contained starting material, as evidenced by TLC. This material was redissolved in methanol (15 ml) and treated with a solution of 'OXONE' (1.50 g, 0.0024 m) in water (10 ml). The mixture was stirred at ambient temperature for 68 hours, then an additional 1.54 g (0.0025 m) of 'OXONE' dissolved in water (10 ml) was added and stirring was continued for 93 hours more. The mixture was filtered, the solid was washed with methanol, and the combined filtrate and washings were concentrated in vacuo below 60° C. to remove methanol. The resultant aqueous solution was extracted with ethyl acetate (3×35 ml), the combined extracts were washed twice with water, dried over sodium sulfate, and concentrated in vacuo. The residue was crystallized from nitromethane to afford 0.36 g (55%) of product melting at 217°–219° C.

EXAMPLE 49

4-Acetoxy-5,6-dihydro-4H-thieno[2,3-b]thiopyran-2-sulfonamide-7,7-dioxide 5,6-Dihydro-4-hydroxy-4H-thieno[2,3-b]thiopyran-2-sulfonamide-7,7-dioxide (2.00 g, 0.0071 m), glacial acetic acid (0.92 g, 0.015 m) and 4-dimethylaminopyridine (0.085 g, 0.0007 m) were dissolved in dry tetrahydrofuran (30 ml) and the solution was cooled to 0° C. under nitrogen and stirred while a solution of dicyclohexylcarbodiimide (1.61 g, 0.0078 m) in dry tetrahydrofuran (10 ml) was added over 10 minutes. After stirring at 0° C. for 1 hour and at ambient temperature for 2 hours, an additional 0.46 g (0.0077 m) of glacial acetic acid was added and stirring was continued at ambient temperature for one hour more. The mixture was filtered and the solid was washed with tetrahydrofuran. The combined filtrate and washings were evaporated in vacuo to give a quantitative yield (2.31 g) of crude product. This material was combined with 1.14 g of identical product from a previous run and chromatographed on silica gel, eluting with 10% methanol-chloroform, to yield 2.57 g (75%) of product. Recrystallization from nitromethane afforded an analytical sample melting at 187.5°–188.5° C.

EXAMPLE 50

5,6-Dihydro-4-(2-hydroxyethoxy)thieno[2,3-b]thiopyran-2-sulfonamide 5,6-Dihydro-4-hydroxythieno[2,3-b]thiopyran-2-sulfonamide, (2.0 g, 0.008 mole) was dissolved in ethylene glycol (20 ml), treated with concentrated hydrochloric acid (10 drops), and stirred at room temperature for 24 hours. The mixture was poured into water (100 ml) and extracted repeatedly with ethyl acetate. Evaporation of the washed and dried ethyl acetate extract left the crude product as an oily solid. Trituration with 10% ethanol in ether followed by recrystallization of the obtained solid (1.35 g) from ethyl acetate gave 885 mg (37%) of product, m.p. 110°–113° C.

EXAMPLE 51

5,6-Dihydro-4-(2-hydroxyethoxy)thieno[2,3-b]thiopyran-2-sulfonamide-7,7-dioxide To a stirred solution of 5,6-dihydro-4-(2-hydroxyethoxy)thieno[2,3-b]thiopyran-2-sulfonamide (1.0 g, 0.0034 mole) in CH$_3$OH (20 ml) was added dropwise a solution of OXONE ® (3.15 g, 0.005 mole) in water (20 ml). The mixture was stirred at ambient temperature overnight and then filtered, washing the filter cake thoroughly with CH$_3$OH. Methanol was stripped from the filtrate in vacuo and the residue was extracted repeatedly with ethyl acetate. Evaporation of the dried extract left the crude product as a yellow gum that was purified by column chromatography on silica gel (75 g, 230–400 mesh). The product was eluted with 90 CHCl$_3$:10CH$_3$OH:1H$_2$O. Evaporation of the eluate left a colorless glass (0.8 g) that was triturated with ether, collected, dried in vacuo, and recrystallized from water. The yield of white crystalline product, m.p. 159°–164° C., was 430 mg (39%).

EXAMPLE 52

5,6-Dihydro-4,5-dihydroxy-4H-thieno[2,3-b]thiopyran-2-sulfonamide-7,7-dioxide

A solution of 6H-thieno[2,3-b]thiopyran-2-sulfonamide-7,7-dioxide (1.15 g, 0.0043 m) in tetrahydrofuran (20 ml) was added to a stirred solution of barium chlorate monohydrate (2.23 g, 0.0069 m) in water (20 ml) under a nitrogen atmosphere. Osmium tetroxide (0.66 g, 0.0026 m) was added and the mixture was stirred at 45° C. for 22 hours. Sodium borohydride (0.16 g, 0.0043 m) was added portionwise and the mixture was stirred at ambient temperature for one hour. After filtering through "Super-Cel", the filtrate was concentrated under reduced pressure at 30° C. to remove tetrahydrofuran, the aqueous suspension was acidified with 6N hydrochloric acid (1.0 ml) and extracted with ethyl acetate (3×75 ml). The combined extracts were washed twice with water, dried over sodium sulfate and concentrated in vacuo to yield 0.81 g (63% yield) of crude product which was purified by chromatography on silica gel, eluting with 15% methanol-chloroform. Recrystallization from nitromethane afforded an analytical sample melting at 182.5°–185° C.

EXAMPLE 53

5,6-Dihydro-4-[2-(ethylamino)ethoxy]thieno[2,3-b]thiopyran-2-sulfonamide-7,7-dioxide

Step A: Preparation of 5,6-Dihydro-4-[2-acetamido)ethoxy]thieno[2,3-b]-thiopyran-2-sulfonamide To a mixture of 5,6-dihydro-4-hydroxythieno[2,3-b]-thiopyran-2-sulfonamide (3.65 g, 0.0145 mole), N-acetylaminoethanol (7 ml) and acetonitrile (28 ml) was added conc. HCl (15 drops). The mixture was stirred at room temperature for 40 days with a second addition of conc. HCl (15 drops) on the seventh day. Solvent was stripped under reduced pressure and the residue was partitioned between ethyl acetate and water. Evaporation of the washed and dried ethyl acetate extract left a mixture of the product and unreacted starting material that was separated by column chromatography on silica gel. The more polar product was eluted with 98 ethyl acetate: 2 methanol (v/v). Evaporation of the eluant left 2.2 g (45%) of off-white solid. A sample recrystallized from acetonitrile melted at 163°–164° C.

Anal. calc'd. for: C$_{11}$H$_{16}$N$_2$O$_4$S$_3$: C, 39.27; H, 4.79; N, 8.33. Found: C, 39.28; H, 4.83; N, 8.39.

Step B: Preparation of 5,6-Dihydro-4-[2-(acetamido)ethoxy]thieno[2,3-b]-thiopyran-2-sulfonamide-7,7-dioxide A solution of 5,6-dihydro-4-[2-(acetamido)ethoxy]-thieno[2,3-b]thiopyran-2-sulfonamide (2.2 g, 0.0065 mole) in methanol (60 ml) was stirred at room temperature while a solution of OXOME ® (5.9 g, 0.0096 mole) in water (50 ml) was added dropwise. The mixture was stirred at room temperature overnight. The precipitate was filtered and washed with methanol. The filtrate was concentrated in vacuo and the residual mixture was extracted with ethyl acetate. Evaporation of the dried (anhydrous Na$_2$SO$_4$) extract left 2.15 g (90%) of white solid product, m.p. 177°–181° C. A sample recrystallized from methanol melted at 183°–185° C.

Anal. calc'd for: C$_{11}$H$_{16}$N$_2$O$_6$S$_3$: C, 35.86; H, 4.38; N, 7.60. Found: C, 35.83; H, 4.48; N, 7.64.

Step C: Preparation of 5,6-Dihydro-4-[2-(ethylamino)ethoxy]thieno[2,3-b]-thiopyran-2-sulfonamide-7,7-dioxide Under nitrogen, a suspension of 5,6-dihydro-4-[2-(acetamido)ethoxy]thieno[2,3-b]thiopyran-2-sulfonamide-7,7-dioxide (2.0 g, 0.0054 mole) in THF (50 ml) was heated to just barely refluxing. Borane methyl sulfide (1.6 ml of 10M solution) was introduced dropwise while methyl sulfide was distilled. Heating was continued for 30 minutes with slow distillaion of THF. The mixture then was evaporated to dryness in vacuo. The residue was treated cautiously with 6N HCl (25 ml). The resulting solution was heated at reflux for 1 hour and then evaporated to dryness in vacuo. The residual oily product was chromatographed on a column of silica gel, the product being eluted with 80 chloroform: 20 methanol: 2 conc. NH$_4$OH (v/v/v). Evaporation of the eluant left the product as a colorless glass that was dried at 46° C. under high vacuum for 20 hours; 1.2 g (63%). The product was converted to the hydrogen oxalate salt by treatment of a solution in absolute ethanol (12 ml) with a solution of oxalic acid (1 equiv.) in ether (25 ml), yield, 1.2 g, m.p. dec. 219°–221° C.

Anal. calc'd for: C$_{11}$H$_{18}$N$_2$O$_5$S$_3$+C$_2$H$_2$O$_4$: C, 35.12; H, 4.54; N, 6.30. Found: C, 35.12; H, 4.61; N, 6.22.

EXAMPLE 54

5,6-Dihydro-4-isobutylamino-4H-thieno[2,3-b]thiopyran-2-sulfonamide-7,7-dioxide-hydrochloride

Step A: Preparation of 5,6-Dihydro-4-isobutyrylamino-4H-thieno[2,3-b]thiopyran-2-sulfonamide-7,7-dioxide Under N$_2$ was added 5,6-dihydro-4-amino-4H-thieno[2,3-b]thiopyran-2-sulfonamide-7,7-dioxidehydrochloride (3.2 g, 0.01 mol), triethylamine (2.2 g, 0.022 mol) and THF (100 ml). The mixture was stirred at room temperature while a solution of isobutyryl chloride (1.12 g, 0.0105 mol) in THF (10 ml) was added dropwise. After 18 hours, the mixture was poured onto saturated NaHCO$_3$ and the suspension was extracted with ethyl acetate (3X). The combined organic extracts were dried, filtered and concentrated to dryness to yield 3.2 g (91%) of product.

Step B: Preparation of 5,6-Dihydro-4-isobutylamino-4H-thieno[2,3-b]thiopyran-2-sulfonamide-7,7-dioxide hydrochloride Under N$_2$ was added 5,6-dihydro-4-isobutyrylamino-4H-thieno[2,3-b]thiopyran-2-sulfonamide-7,7-dioxide (3.0 g, 0.0085 mol) in THF (80 ml). The flask was fitted with a short path distillation head and the mixture was heated at reflux while a solution of borane dimethylsulfide (2.6 ml of 10M, 0.020 mol) was added dropwise with stirring (the short path distillation head was utilized to collect the volatile dimethylsulfide). After 1.5 hour, the reaction mixture was concentrated to dryness, the residue was treated with 12N HCl an the mixture heated at reflux. After 0.5 hour, the suspension was concentrated to dryness. The residue was treated with saturated NaHCO$_3$ and the mixture was extracted with ethyl acetate (3X). The organic layer was dried, filtered and concentrated to dryness. The residue was chromatographed on silical gel (230–400 mesh) and the product eluted with 10% $CH_3OH$-$CHCl_3$ saturated with $NH_3$. The product was crystallized as the HCl salt from ethanol to yield, 1.7 g (53%) of product, m.p. 262°–264° C.

EXAMPLE 55

5,6-Dihydro-4-n-butylamino-4H-thieno[2,3-b]thiopyran-2-sulfonamide-7,7-dioxide hydrochloride Employing the procedures substantially as described in Example 54, but substituting for the isobutyryl chloride used in Step A thereof an equimolar amount of n-butyryl chloride, there are produced in sequence:

5,6-dihydro-4-n-butyrylamino-4H-thieno[2,3-b]thiopyran-2-sulfonamide-7,7-dioxide; and 5,6-dihydro-4-n-butylamino-4H-thieno[2,3-b]thiopyran-2-sulfonamide hydrochloride, m.p. 285°–287° C. ($CH_3OH$).

Employing the procedures substantially as described in the foregoing examples and other procedures well known in the art there are produced the compounds described in the following Table.

| Isomer | X | Y | n | $R^1$ | $R^2$ | $R^3$ | $R^4$ |
|---|---|---|---|---|---|---|---|
| [2,3-b] | S | S | 1 | —O— | | —$C_2H_5$ | —$C_2H_5$ |
| [3,2-b] | S | S | 1 | —NHSNH$_2$ (S=O) | H | H | H |
| [2,3-b] | SO | S | 1 | —NHSO$_2$CH$_3$ | H | H | H |
| [3,2-b] | SO$_2$ | S | 1 | —OCNH$_2$ (C=O) | H | H | H |
| [3,2-b] | S | S | 1 | —CH$_2$CN | H | H | H |
| [3,2-b] | SO$_2$ | S | 1 | —CH$_2$CO$_2$Et | H | H | H |
| [2,3-b] | S | S | 1 | —CH$_2$CONH$_2$ | H | H | H |
| [2,3-b] | SO | S | 1 | —CH$_2$CH$_2$NH$_2$ | H | H | H |
| [2,3-b] | SO$_2$ | S | 1 | —CH$_2$CH$_2$OH | H | H | H |
| [3,2-b] | SO$_2$ | S | 1 | —OH | H | OH | H |
| [2,3-b] | S | S | 1 | —OH | H | —N($C_2H_5$)$_2$ | H |
| [3,2-b] | SO$_2$ | S | 1 | —OH | H | H | H |
| [2,3-b] | SO$_2$ | S | 1 | —OH | H | H | H |
| [2,3-b] | SO$_2$ | O | 1 | H | CH$_2$OH | H | H |
| [2,3-b] | SO$_2$ | O | 1 | H | OH | H | H |
| [2,3-b] | S | S | 1 | H | CH$_2$OH | H | H |
| [2,3-b] | SO$_2$ | S | 1 | —CH$_2$CH$_2$OH | H | H | H |
| [2,3-b] | S | S | 2 | OH | H | N(CH$_3$)$_2$ | H |
| [3,2-b] | SO$_2$ | S | 2 | OH | H | OH | H |
| [2,3-b] | SO$_2$ | S | 1 | OC(CH$_2$)$_2$NH$_2$ (C=O) | H | H | H |
| [2,3-b] | SO$_2$ | S | 1 | OCCH$_2$CH$_2$OH (C=O) | H | H | H |
| [3,2-b] | SO$_2$ | S | 1 | OCCH$_2$CH$_2$CO$_2$H (C=O) | H | H | H |
| [2,3-b] | SO$_2$ | S | 1 | OC-(3-pyridyl) (C=O) | H | H | H |
| [2,3-b] | SO$_2$ | S | 1 | SO$_2$CH$_3$ | H | H | H |
| [3,2-b] | SO$_2$ | S | 1 | H | H | H | H |
| [3,2-b] | SO$_2$ | NH | 1 | OH | H | H | H |
| [2,3-b] | SO$_2$ | NH | 1 | OH | H | H | H |
| [2,3-b] | S | S | 1 | SO$_2$NH$_2$ | H | H | H |
| [3,2-b] | SO$_2$ | S | 1 | OCH$_2$CH$_2$NEt$_2$ | H | H | H |

-continued

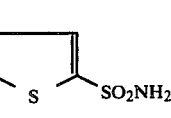

| Isomer | X | Y | n | R¹ | R² | R³ | R⁴ |
|---|---|---|---|---|---|---|---|
| [2,3-b] | $SO_2$ | S | 1 | 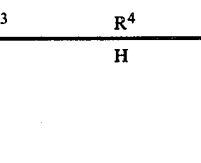 | H | H | H |
| [3,2-b] | S | S | 1 | $CH_3$ | H | H | H |
| [2,3-b] | $SO_2$ | S | 1 | $CH_2OH$ | OH | $CH_3$ | $CH_3$ |
| [2,3-b] | $SO_2$ | S | 1 | Cl | = | = | H |
| [2,3-b] | $SO_2$ | S | 1 | $NHCH_3$ | H | OH | H |
| [2,3-b] | $SO_2$ | S | 1 | $NH_2$ | H | H | OH |

The following examples of ophthalmic formulations are given by way of illustration.

EXAMPLE 56

| | | |
|---|---|---|
| 5,6-dihydro-4H—4-hydroxythieno[2,3-b]thiopyran-2-sulfonamide-7,7-dioxide | 1 mg | 15 mg |
| Monobasic sodium phosphate $2H_2O$ | 9.38 mg | 6.10 mg |
| Dibasic sodium phosphate.$12H_2O$ | 28.48 mg | 16.80 mg |
| Benzalkonium chloride | 0.10 mg | 0.10 mg |
| Water for injection q.s. ad. | 1.0 ml | 1.0 ml |

The novel compound, phosphate buffer salts, and benzalkonium chloride are added to and dissolved in water. The pH of the composition is adjusted to 6.8 and diluted to volume. The composition is rendered sterile by ionizing radiation.

EXAMPLE 57

| | |
|---|---|
| 6,7-dihydro-5H—7-hydroxythieno[3,2-b]thiopyran-2-sulfonamide-7,7-dioxide | 5 mg |
| petrolatum q.s. ad. | 1 gram |

The compound and the petrolatum are aseptically combined.

EXAMPLE 58

| | |
|---|---|
| 5,6-dihydro-4H—4-hydroxythieno[2,3-b]thiopyran-2-sulfonamide-7,7-dioxide | 1 mg |
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A compound of structural formula:

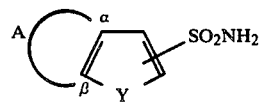

wherein A together with the two carbon atoms denoted as a and β is the group:

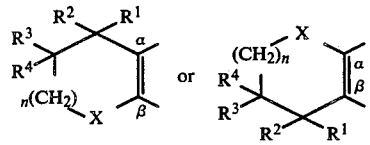

wherein
n is 1 or 2;
X is —S—, —SO—, —$SO_2$—;
Y is —S—;
R¹, R², R³, R⁴ are independently selected from:
  (1) hydrogen,
  (2) OR⁵ wherein R⁵ is:
    (a) hydrogen,
    (b) $C_{1-5}$ alkyl, either unsubstituted or substituted with

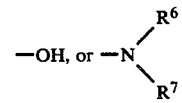

wherein R⁶ and R⁷ are independently hydrogen or $C_{1-5}$ alkyl,
    (c) $C_{1-5}$ alkanoyl, either unsubstituted or substituted with —OH, —NR⁶R⁷ or —COR⁸ wherein R⁸ is —OH, —NR⁶R⁷ or $C_{1-5}$ alkoxy,
    (d) —CO—R⁹, wherein R⁹ is —NR⁶R⁷
  (3) —NR⁶R⁷,
  (4) —NHR¹⁰ wherein R¹⁰ is:
    (a) —$SO_2$NR⁶R⁷,
    (b) —$SO_2$R¹¹, wherein R¹¹ is $C_{1-5}$ alkyl, or
    (c) —CONR⁶R⁷,
  (5) $C_{1-5}$ alkyl, either unsubstituted or substituted with
    (a) —OR⁵,
    (b) —CN, (c) —NR$^6$R$^7$, or
(d) —COR$^8$,
(6) —SO$_2$R$^{11}$,
(7) —SO$_2$NR$^6$R$^7$, or
(8) —halo;

R$^1$ and R$^3$, or R$^2$ and R$^4$ taken together represent a double bond;

R$^1$ and R$^2$, or R$^3$ and R$^4$ taken together represent
(1) =O, or
(2) =NOR$^{12}$ wherein R$^{12}$ is hydrogen or C$_{1-3}$ alkyl; and one of the —CH$_2$— groups of —(CH$_2$)$_n$— can be substituted with —COR$^8$, —CH$_2$R$^8$ or —CH$_2$COR$^8$.

2. The compound of claim 1, wherein Y is S.

3. The compound of claim 2, wherein X is —S— or —SO$_2$—.

4. The compound of claim 3 wherein n is 1, R$^2$ is hydrogen, R$^3$ and R$^4$ are hydrogen or C$_{1-5}$ alkyl, and R$^1$ is —OH, —CH$_2$OH, or —NR$^6$R$^7$.

5. The compound of claim 4 which is
5,6-dihydro-4H-4-hydroxythieno[2,3-b]thiopyran-2-sulfonamide-7,7-dioxide;
5,6-dihydro-4H-4-hydroxythieno[2,3-b]thiopyran-2-sulfonamide;
6,7-dihydro-5H-7-hydroxythieno[3,2-b]thiopyran-2-sulfonamide;
6,7-dihydro-5H-7-hydroxythieno[3,2-b]thiopyran-2-sulfonamide-4,4-dioxide;
5,6-dihydro-4H-4-(N-ethylamino)thieno[2,3-b]thiopyran-2-sulfonamide-7,7-dioxide;
5,6-dihydro-4H-4-aminothieno[2,3-b]thiopyran-2-sulfonamide-7,7-dioxide;
5,6-dihydro-4-hydroxy-5,5-dimethyl-4H-thieno[2,3-b]thiopyran-2-sulfonamide-7,7-dioxide;
5,6-dihydro-4H-4-hydroxymethylthieno[2,3-b]thiopyran-2-sulfonamide-7,7-dioxide;
5,6-dihydro-4-isobutylamino-4H-thieno[2,3-b]thiopyran-2-sulfonamide-7,7-dioxide; or
5,6-dihydro-4-n-butylamino-4H-thieno[2,3-b]thiopyran-2-sylfonamide-7,7-dioxide.

6. The compound of claim 4 which is 5,6-dihydro-4H-4-hydroxythieno[2,3-b]thiopyran-2-sulfonamide-7,7-dioxide.

7. The compound of claim 4 which is 5,6-dihydro-4-isobutylamino-4H-thieno[2,3-b]thiopyran-2-sulfonamide-7,7-dioxide.

8. The compound of claim 4 which is 5,6-dihydro-4H-4-aminothiieno[2,3-b]thiopyran-2-sulfonamide-7,7-dioxide.

9. The compound of claim 4 which is 5,6-dihydro-4-hydroxy-5,5-dimethyl-4H-thieno[2,3-b]thiopyran-2-sulfonamide-7,7-dioxide.

10. 5,6-dihydro-4H-4-hydroxymethylthieno-[2,3-b]thiopyran-2-sulfonamide-7,7-dioxide.

11. (S,R)- and (R,R)-5,6-Dihydro-4-[2-methoxy-2-phenylacetoxy]thieno[2,3-b]thiopyran-2-sulfonamide-7,7-dioxide.

12. An ophthalmic composition for the treatment of elevated intracular pressure comprising an ophthalmologically acceptable carrier and an effective intracular pressure lowering amount of a compound defined in claim 1.

13. The composition of claim 12 wherein Y is S.

14. The composition of claim 12 wherein Y is —S—, and X is —S— or —SO$_2$—.

15. The composition of claim 12 wherein Y is —S—, X is —S— or —SO$_2$—, n is 1, R$^2$ is hydrogen, R$^3$ and R$^4$ are hydrogen or C$_{1-5}$ alkyl, and R$^1$ is —OH, —CH$_2$OH, or NR$^6$R$^7$.

16. The commposition of claim 12 wherein the compound is:
5,6-dihydro-4H-4-hydroxythieno[2,3-b]thiopyran-2-sulfonamide-7,7-dioxide;
5,6-dihydro-4H-4-hydroxythieno[2,3-b]thiopyran-2-sulfonamide;
6,7-dihydro-5H-7-hydroxythieno[3,2-b]thiopyran-2-sulfonamide;
6,7-dihydro-5H-7-hydroxythieno[3,2-b]thiopyran-2-sulfonamide-4,4-dioxide;
5,6-dihydro-4H-4-(N-ethylamino)thieno[2,3-b]thiopyran-2-sulfonamide-7,7-dioxide;
5,6-dihydro-4H-4-aminothieno[2,3-b]thiopyran-2-sulfonamide-7,7-dioxide;
5,6-dihydro-4-hydroxy-5,5-dimethyl-4H-thieno[2,3-b]thiopyran-2-sulfonamide-7,7-dioxide;
5,6-dihydro-4H-4-hydroxymethylthieno[2,3-b]thiopyran-2-sulfonamide-7,7-dioxide;
5,6-dihydro-4-isobutylamino-4H-thieno[2,3-b]thiopyran-2-sulfonamide-7,7-dioxide; or
5,6-dihydro-4-n-butylamino-4H-thieno[2,3-b]thiopyran-2-sulfonamide-7,7-dioxide.

17. The composition of claim 12 wherein the compound is 5,6-dihydro-4H-4-hydroxythieno[2,3-b]thiopyran-2-sulfonamide-7,7-dioxide.

18. The composition of claim 12 wherein the compound is 5,6-dihydro-4-isobutylamino-4H-thieno[2,3-b]thiopyran-2-sulfonamide-7,7-dioxide.

19. The composition of claim 12 wherein the compound is 5,6-dihydro-4H-4-aminothieno[2,3-b]thiopyran-2-sulfonamide-7,7-dioxide.

20. The composition of claim 12 wherein the compound is 5,6-dihydro-4-hydroxy-5,5-dimethyl-4H-thieno[2,3-b]-thiopyran-2-sulfonamide-7,7-dioxide.

21. The composition of claim 12 wherein the compound is 5,6-dihydro-4H-4-hydroxymethylthieno[2,3-b]thiopyran-2-sulfonamide-7,7-dioxide.

22. A method of treating elevated intraocular pressure, including glaucoma, which comprises the topical optical administration of an effective intraocular pressure lowering amount of a compound as defined in claim 1.

23. The method of claim 22, wherein Y is —S—.

24. The method of claim 22, wherein Y is —S—, and X is —S— or —SO$_2$—.

25. The method of claim 22, wherein Y is —S—, X is —S— or —SO$_2$—, n is 1, R$^2$ is hydrogen, R$^3$ and R$^4$ are hydrogen or C$_{1-4}$ alkyl, and R$^1$ is —OH, —CH$_2$OH or NR$^6$R$^7$.

26. The method of claim 22 wherein the compound is:
5,6-dihydro-4H-4-hydroxythieno[2,3-b]thiopyran-2-sulfonamide-7,7-dioxide;
5,6-dihydro-4H-4-hydroxythieno[2,3-b]thiopyran-2-sulfonamide;
6,7-dihydro-5H-7-hydroxythieno[3,2-b]thiopyran-2-sulfonamide;
6,7-dihydro-5H-7-hydroxythieno[3,2-b]thiopyran-2-sulfonamide-4,4-dioxide;
5,6-dihydro-4H-4-(N-ethylamino)thieno[2,3-b]thiopyran-2-sulfonamide-7,7-dioxide;
5,6-dihydro-4H-4-aminothieno[2,3-b]thiopyran-2-sulfonamide-7,7-dioxide;
5,6-dihydro-4-hydroxy-5,5-dimethyl-4H-thieno[2,3-b]thiopyran-2-sulfonamide-7,7-dioxide;
5,6-dihydro-4H-4-hydroxymethylthieno[2,3-b]thiopyran-2-sulfonamide-7,7-dioxide;

5,6-dihydro-4-isobutylamino-4H-thieno[2,3-b]thiopyran-2-sulfonamide-7,7-dioxide; or
5,6-dihydro-4-n-butylamino-4H-thieno[2,3-b]thiopyran-2-sulfonamide-7,7-dioxide.

27. The method of claim 22 wherein the compound is 5,6-dihydro-4H-4-hydroxythieno[2,3-b]thiopyran-2-sulfonamide-7,7-dioxide.

28. The method of claim 22 wherein the compound is 5,6-dihydro-4-isobutylamino-4H-thieno[2,3-b]thiopyran-2-sulfonamide-7,7-dioxide.

29. The method of claim 22 wherein the compound is 5,6-dihydro-4H-4-aminothieno[2,3-b]thiopyran-2-sulfonamide-7,7-dioxide.

30. The method of claim 22 wherein the compound is 5,6-dihydro-4-hydroxy-5,5-dimethyl-4H-thieno[2,3-b]thiopyran-2-sulfonamide-7,7-dioxide.

31. The method of claim 22 wherein the compound is 5,6-dihydro-4H-4-hydroxymethylthieno[2,3-b]thiopyran-2-sulfonamide-7,7-dioxide.

* * * * *

REEXAMINATION CERTIFICATE (1843rd)

United States Patent [19]

Baldwin et al.

[11] B1 4,677,115

[45] Certificate Issued Nov. 10, 1992

[54] ANTIGLAUCOMA THIENO-THIOPYRAN AND THIENO-THIEPIN SULFONAMIDE DERIVATIVES, COMPOSITIONS AND METHOD OF USE THEREOF

[75] Inventors: John J. Baldwin, Gwynedd Valley; Marcia E. Christy, Collegeville; Gerald S. Ponticello, Lansdale, all of Pa.

[73] Assignee: Merck & Co., Inc., Rahway, N.J.

Reexamination Request:
No. 90/002,681, Mar. 23, 1992

Reexamination Certificate for:
Patent No.: 4,677,115
Issued: Jun. 30, 1987
Appl. No.: 863,225
Filed: May 14, 1986

Related U.S. Application Data

[63] Continuation-in-part of Ser. No. 777,654, Sep. 19, 1985, which is a continuation-in-part of Ser. No. 680,684, Dec. 12, 1984, abandoned.

[51] Int. Cl.$^5$ ................... A61K 31/38; C07D 495/04
[52] U.S. Cl. ................... 514/432; 514/431; 549/9; 549/23

[56] References Cited

U.S. PATENT DOCUMENTS 4,619,939 10/1986 Maren ......................... 514/363

*Primary Examiner*—Robert W. Ramsuer

[57] ABSTRACT

Aromatic sulfonamides with a saturated heterocycle fused thereto are carbonic anhydrase inhibitors useful in the treatment of elevated intraocular pressure.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-31 is confirmed.

* * * * *